(12) United States Patent
Nemoto et al.

(10) Patent No.: US 7,696,359 B2
(45) Date of Patent: Apr. 13, 2010

(54) COMPOUND MODIFIED WITH GLYCEROL DERIVATIVE

(75) Inventors: Hisao Nemoto, Tokushima (JP); Masahiro Yamauchi, Shizuoka (JP); Hiroko Kusano, Tokyo (JP); Yasuki Kato, Shiozuoka (JP); Motoo Yamasaki, Tokyo (JP); Toshiyuki Suzawa, Tokyo (JP)

(73) Assignees: Kyowa Hakko Kirin Co., Ltd., Tokyo (JP); Techno Network Shikoku Co., Ltd., Kagawa (JP)

( * ) Notice: Subject to any disclaimer, the term of this patent is extended or adjusted under 35 U.S.C. 154(b) by 511 days.

(21) Appl. No.: 10/570,623

(22) PCT Filed: Sep. 3, 2004

(86) PCT No.: PCT/JP2004/013187

§ 371 (c)(1),
(2), (4) Date: Mar. 3, 2006

(87) PCT Pub. No.: WO2005/023844

PCT Pub. Date: Mar. 17, 2005

(65) Prior Publication Data

US 2006/0280784 A1    Dec. 14, 2006

(30) Foreign Application Priority Data

Sep. 3, 2003    (JP)    ............... 2003-311436

(51) Int. Cl.
C07D 207/46    (2006.01)
C07F 9/09    (2006.01)
(52) U.S. Cl. .................................. 548/542; 558/70
(58) Field of Classification Search .................. 548/542
See application file for complete search history.

(56) References Cited

U.S. PATENT DOCUMENTS

| | | | | |
|---|---|---|---|---|
| 5,013,556 | A | 5/1991 | Woodle et al. | 424/450 |
| 5,552,391 | A * | 9/1996 | Coutts et al. | 514/44 R |
| 5,593,622 | A | 1/1997 | Yoshioka | 264/4.32 |
| 6,132,763 | A | 10/2000 | Fisher | 424/450 |
| 2005/0208015 | A1 | 9/2005 | Nemoto et al. | 424/85.1 |

FOREIGN PATENT DOCUMENTS

| JP | 6-228012 | 8/1994 |
|---|---|---|
| JP | 8-325271 | 12/1996 |

OTHER PUBLICATIONS

Song, et al., "Characterization of the inhibitory effect of PEG-lipid conjugates on the . . . ", *Biochimica et Biophysica Acta*, vol. 1558 (2002), pp. 1-13.
Ishida, et al., "Accelerated clearance of PEGylated liposomes in rats after repeated injections", *Journal of Controlled Release*, vol. 88 (2003), pp. 35-42.
Dams, et al., "Accelerated Blood Clearance and Altered Biodistribution of Repeated Injections of . . . ", *The Journal of Pharmacology and Experimental Therapeutics*, vol. 292, No. 3 (2000), pp. 1071-1079.
Klibanov, et al., "Activity of amphipathic poly(ethylene glycol) 5000 to prolong the cirulation time of . . . ", *Biochimica et Biophysica Acta*, vol. 1062 (1991), pp. 142-148.
Cassel, et al., "Original Synthesis of Linear, Branched and Cyclic Oligoglycerol Standards", *Eur. J. Org. Chem.*, vol. 5 (2001), pp. 875-896.
Zhong, et al., "Photochemistry on Soluble Polymer Supports: Synthesis of Nucleosides", *Org. Lett.*, vol. 4, No. 25 (2002), pp. 4415-4417.
Das, et al., "Synthesis of water soluble boron neutron capture theraphy agent: . . . ", *Journal of Organometallic Chemistry*, vol. 614-615 (2000), pp. 255-261.
Nemoto, et al., "Design and Synthesis of Cholestane Derivatives Bearing a Cascade-type Polyol and the . . . ", *Bioorganic & Medicinal Chemistry Letters*, vol. 9 (1999), pp. 205-208.
Carnahan, et al., "Synthesis and Characterization of Poly(glycerol-succinic acid) Dendrimers", *Macromolecules*, vol. 34 (2001), pp. 7648-7655.

(Continued)

*Primary Examiner*—Kamal A Saeed
*Assistant Examiner*—Shawquia Young
(74) *Attorney, Agent, or Firm*—Fitzpatrick, Cella, Harper & Scinto

(57) ABSTRACT

Objects of the present invention are to provide a compound which is useful as a surface modifier for producing a drug carrier or the like, or a salt thereof; a fine particle comprising the same; and the like. The present invention provides a compound in which a substance to be modified, which is selected from the group consisting of an amphiphilic substance and a hydrophobic substance, is modified with a glycerol derivative represented by the following formula (1):

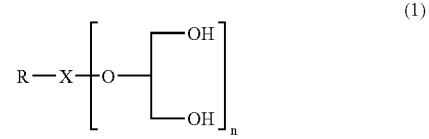

wherein R represents a residue comprising a reactive group for the substance to be modified, which is selected from the group consisting of an amphiphilic substance and a hydrophobic substance or for a spacer capable of binding the substance to be modified, which is selected from the group consisting of an amphiphilic substance and a hydrophobic substance, to R-X, or a group capable of being transformed into the reactive group; n represents an integer of 3 or more; and X represents a residue capable of having the following structure by n in number:

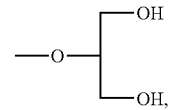

directly or via the spacer, or a salt thereof; a fine particle comprising the same; and the like.

9 Claims, No Drawings

OTHER PUBLICATIONS

Morgan, et al., "Divergent Synthesis of Biodendrimers from Glycerol and Caproic Acid", *Polymer Preprints*, vol. 42, No. 2 (2001), pp. 155-156.

Carnahan, et al., "Biologically Inspired Dendrimers Based on Glycerol and Succinic Acid", *Polymer Preprints*, vol. 42, No. 2 (2001), pp. 157-158.

Carnahan, et al., "Synthesis and Characterization of Polyether-Ester Dendrimers from Glycerol and Lactic Acid", *J. Am. Chem. Soc.*, vol. 123 (2001), pp. 2905-2906.

Grayson, et al., "Synthesis and Surface Functionalization of Aliphatic Polyether Dendrons", *J. Am. Chem. Soc.*, vol. 122 (2000), pp. 10335-10344.

Ling-Ling, et al., "A facile convergent route to dendritic polyols", *Chinese Journal of Chemistry*, vol. 16, No. 1 (1998), pp. 28-33.

Malefant, et al., "Dendrimers as Solubilizing Groups for Conducting Polymers: Preparation and . . .", *Macromolecules*, vol. 33 (2000), pp. 3634-3640.

Malefant, et al., "Dendrimer-Supported Oligothiophene Synthesis: Aliphatic Ether Dendrimers in the . . .", *Chem. Mater.*, vol. 11 (1999), pp. 3420-3422.

Malenfant, et al., "Dendrimer-Supported Solution Synthesis of . . .", *Polymeric Materials Science and Engineering*, vol. 80 (1999), pp. 171-172.

* cited by examiner

COMPOUND MODIFIED WITH GLYCEROL DERIVATIVE

TECHNICAL FIELD

The present invention relates to a compound in which an amphiphilic substance or a hydrophobic substance is modified with a glycerol derivative, which is useful as a surface modifier for producing a drug carrier or the like, or a salt thereof; a fine particle comprising the same; and the like.

BACKGROUND ART

As drug delivery systems for transferring a necessary amount of an administered drug to a desired tissue when needed, methods using a fine particles such as a liposome, an emulsion, a micell, a fine particle crystal, a microcapsule, a microsphere or the like as a drug carrier are known.

For example, liposomes are used as drug carriers for antitumor agents, antiinflammatory agents and the like. It is known that, when administered into a vein, the liposomes are trapped in the lung, liver, spleen or the like and rapidly disappear from blood. Therefore, it is difficult for the liposomes to efficiently transfer the agents to a tumor or inflamed part in a target region other than the lung, liver, and spleen. Thus, various attempts have been made to increase retention of the liposomes in blood, including chemical modification of the liposomes with polyethylene glycol (PEG), and the like. For example, it is known that liposomes modified with surface modifiers comprising PEG derivatives (PEG-modified liposomes) show remarkably high retention in blood (for example, Japanese Patent No. 2667051, Japanese Published Examined Patent Application No. 20857/95, Japanese Patent No. 2948246 and the like). Also, it is known that liposomes modified with surface modifiers comprising polyglycerin derivatives (polyglycerin-modified liposomes) are increased retention in blood (for example, Japanese Published Unexamined Patent Application No. 228012/94).

However, the PEG-modified liposomes have several disadvantages in view of use as the drug carrier. For example, although a PEG-modified liposome can efficiently transfer a drug to a tumor cell, the PEG on the surface of the liposome has a large steric hindrance to inhibit interaction between the drug and the tumor cell to thereby prevent the drug from efficiently moving into the tumor cell (*Biochimica et Biophysica Acta*, 1558, 1-13 (2002)). Also, it is known that when a PEG-modified liposome is repeatedly administered, the retention thereof in blood is reduced (*Journal of Controlled Release*, 88, 35-42 (2003) and *Journal of Pharmacology and Experimental Therapeutics*, 292, 1071-1079 (2000)). Furthermore, in a PEG-modified liposome containing a monoclonal antibody, the PEG inhibits the cell recognition ability of the antibody, whereby there is a difficulty in active targeting by the PEG-modified liposome (*Biochimica et Biophysica Acta*, 1062, 142-148 (1991)). Moreover, it is possible that the stability of a liposome membrane is reduced by introducing a PEG to a lipid of the liposome, whereby a drug encapsulated in the liposome easily leaks.

Although the polyglycerin-modified liposomes have been developed as ones with high retention in blood instead of the PEG-modified liposomes, they are insufficient in the retention, which is only twice as high as unmodified liposomes.

Under such circumstances, there is a demand for a novel drug carrier as a substitute to the PEG-modified liposomes.

DISCLOSURE OF THE INVENTION

Objects of the present invention are to provide a compound in which an amphiphilic substance or a hydrophobic substance is modified with a glycerol derivative, which is useful as a surface modifier for producing a drug carrier or the like, or a salt thereof; a fine particle comprising the same; and the like. In the present invention, a surface modifier is one of components of a drug carrier such as a fine particle, and is a compound in which a part or the whole of the structure of the surface of the carrier is extended outward from the carrier or a composition comprising the compound.

The present invention relates to the following (1) to (28).

(1) A compound in which a substance to be modified, which is selected from the group consisting of an amphiphilic substance and a hydrophobic substance, is modified with a glycerol derivative represented by the following formula (1):

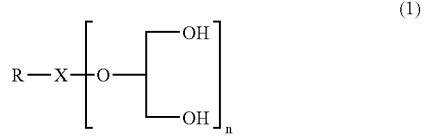

wherein R represents a residue comprising a reactive group for the substance to be modified, which is selected from the group consisting of an amphiphilic substance and a hydrophobic substance or for a spacer capable of binding the substance to be modified, which is selected from the group consisting of an amphiphilic substance and a hydrophobic substance, to R-X, or a group capable of being transformed into the reactive group; n represents an integer of 3 or more; and X represents a residue capable of having the following structure by n in number:

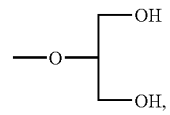

directly or via the spacer,
or a salt thereof.

(2) The compound according to the above-described (1), wherein n is $2^m$, in which m is an integer of 2 or more, or a salt thereof.

(3) The compound according to the above-described (1) or (2), wherein X comprises one or more series branched structure(s), or a salt thereof.

(4) The compound according to any one of the above-described (1) to (3), wherein X comprises one to (n−1) structure(s) represented by

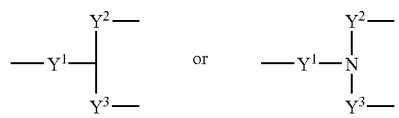

wherein $Y^1$, $Y^2$ and $Y^3$ each independently represents a single bond, or one, or two or more in any combination, which may be the same or different, selected from the group consisting of substituted or unsubstituted alkylene, carbonyl, substituted or unsubstituted imino, O, S, sulfonyl and sulfinyl, and when $Y^1$, $Y^2$ and $Y^3$ exist two or more in number, they may be the same or different,
or a salt thereof.

(5) The compound according to any one of the above-described (1) to (4), wherein X comprises one to (n−1) structure(s) represented by

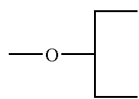

or a salt thereof.

(6) The compound according to any one of the above-described (1) to (5), wherein X comprises one to (n−1) structure(s) represented by

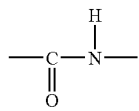

or a salt thereof.

(7) The compound according to any one of the above-described (1) to (6), wherein X comprises one to (n−1) structure(s) represented by

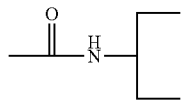

or a salt thereof.

(8) The compound according to any one of the above-described (1) to (7), wherein X comprises one to (n−1) structure(s) represented by

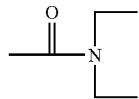

or a salt thereof.

(9) The compound according to any one of the above-described (1) to (8), wherein R is a residue comprising a reactive group for a group selected from the group consisting of carboxy, amino, a hydroxyl group, mercapto, formyl, a sulfuric acid residue, a phosphoric acid residue, a phosphonic acid residue and partial structures thereof in the substance to be modified, which is selected from the group consisting of an amphiphilic substance and a hydrophobic substance, or the spacer capable of binding the substance to be modified, which is selected from the group consisting of an amphiphilic substance and a hydrophobic substance, to R-X, or a group capable of being transformed into the reactive group.

(10) The compound according to any one of the above-described (1) to (8), wherein R is selected from the group consisting of a carboxylic acid active ester residue, carbonate, maleimido, mercapto, formyl, tresyl, isocyanato, an acid anhydride residue, an acid halide residue, vinylsulfonyl, hydrazido, amino, a hydroxyl group, halogen, carboxy, vinyl and phosphono, or a salt thereof.

(11) A mixture comprising at least two of the compounds according to any one of the above-described (1) to (10) and salts thereof.

(12) The compound according to any one of the above-described (1) to (11), wherein the substance to be modified, which is selected from the group consisting of an amphiphilic and a hydrophobic substance is a lipid or a derivative thereof, or a salt thereof.

(13) A compound represented by the following formula (2):

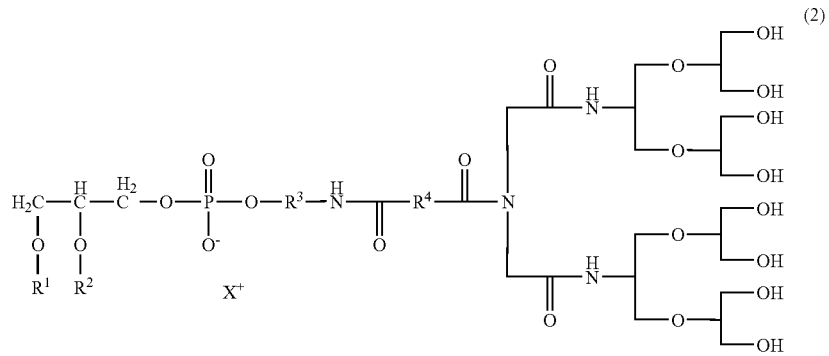

wherein X represents a hydrogen atom or an alkaline metal atom; $R^1$ and $R^2$, which may be the same or different, each represent a hydrogen atom, a saturated fatty acid residue or an unsaturated fatty acid residue, and at least one of $R^1$ and $R^2$ is the saturated fatty acid residue or the unsaturated fatty acid residue; and $R^3$ and $R^4$, which may be the same or different, each represent alkylene having 1 to 10 carbon atoms, or a salt thereof.

(14) A compound represented by the following formula (3):

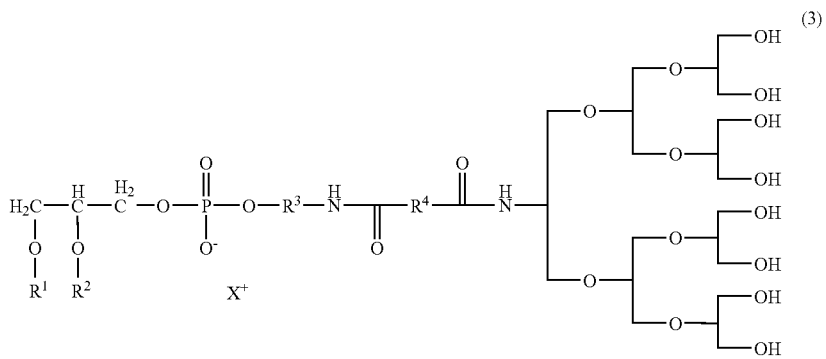

wherein X represents a hydrogen atom or an alkaline metal atom; $R^1$ and $R^2$, which may be the same or different, each represent a hydrogen atom, a saturated fatty acid residue or an unsaturated fatty acid residue, and at least one of $R^1$ and $R^2$ is the saturated fatty acid residue or the unsaturated fatty acid residue; and $R^3$ and $R^4$, which may be the same or different, each represent alkylene having 1 to 10 carbon atoms, or a salt thereof.

(15) A compound represented by the following formula (4):

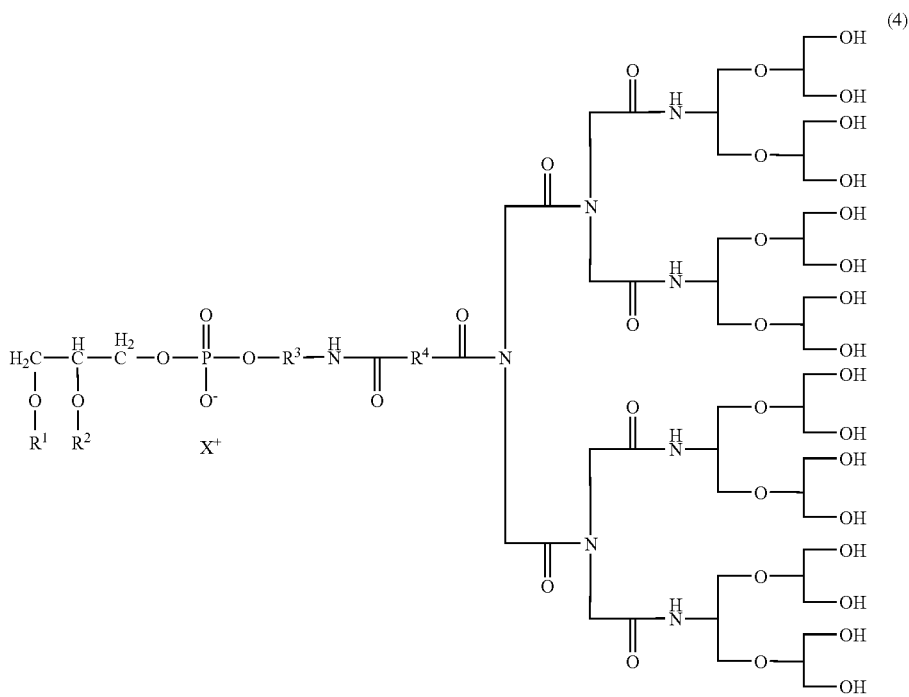

wherein X represents a hydrogen atom or an alkaline metal atom; $R^1$ and $R^2$, which may be the same or different, each represent a hydrogen atom, a saturated fatty acid residue or an unsaturated fatty acid residue, and at least one of $R^1$ and $R^2$ is the saturated fatty acid residue or the unsaturated fatty acid residue; and $R^3$ and $R^4$, which may be the same or different, each represent alkylene having 1 to 10 carbon atoms, or a salt thereof

(16) A compound represented by the following formula (5):

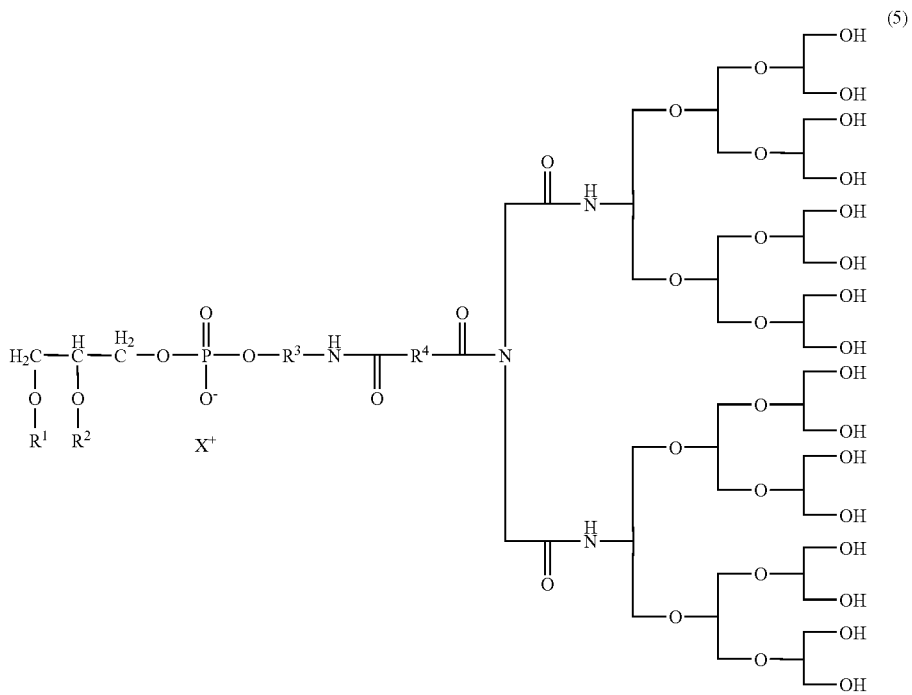

wherein X represents a hydrogen atom or an alkaline metal atom; $R^1$ and $R^2$, which may be the same or different, and each represent a hydrogen atom, a saturated fatty acid residue or an unsaturated fatty acid residue, and at least one of $R^1$ and $R^2$ is the saturated fatty acid residue or the unsaturated fatty acid residue; and $R^3$ and $R^4$, which may be the same or different, each represent alkylene having 1 to 10 carbon atoms, or a salt thereof.

(17) A compound represented by the following formula (6):

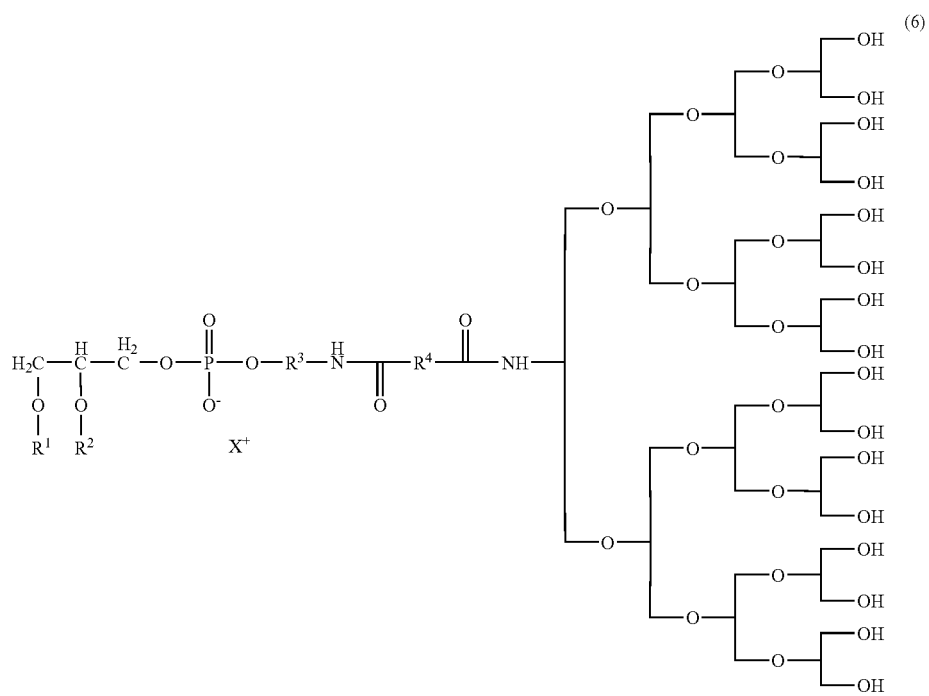

wherein X represents a hydrogen atom or an alkaline metal atom; $R^1$ and $R^2$, which may be the same or different, and each represent a hydrogen atom, a saturated fatty acid residue or an unsaturated fatty acid residue, and at least one of $R^1$ and $R^2$ is the saturated fatty acid residue or the unsaturated fatty acid residue; and $R^3$ and $R^4$, which may be the same or different, each represent alkylene having 1 to 10 carbon atoms, or a salt thereof.

(18) A compound represented by the following formula (7):

wherein X represents a hydrogen atom or an alkaline metal atom; $R^1$ and $R^2$, which may be the same or different, each represent a hydrogen atom, a saturated fatty acid residue or an unsaturated fatty acid residue, and at least one of $R^1$ and $R^2$ is the saturated fatty acid residue or the unsaturated fatty acid residue; and $R^3$ and $R^4$, which may be the same or different, each represent alkylene having 1 to 10 carbon atoms, or a salt thereof.

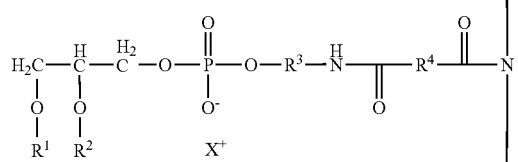
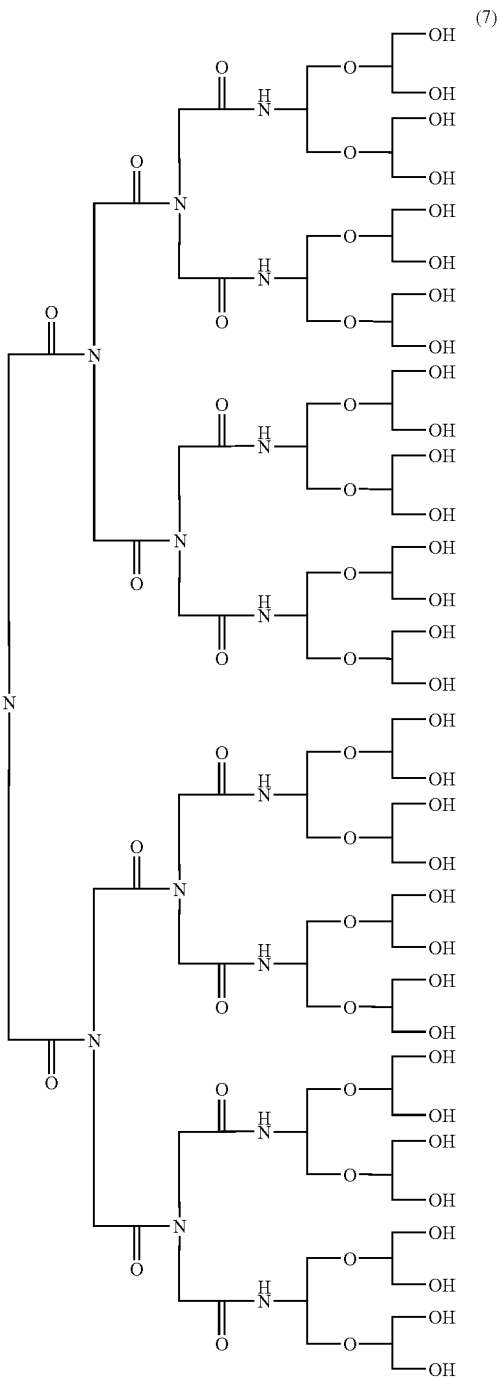

(19) A compound represented by the following formula (8):

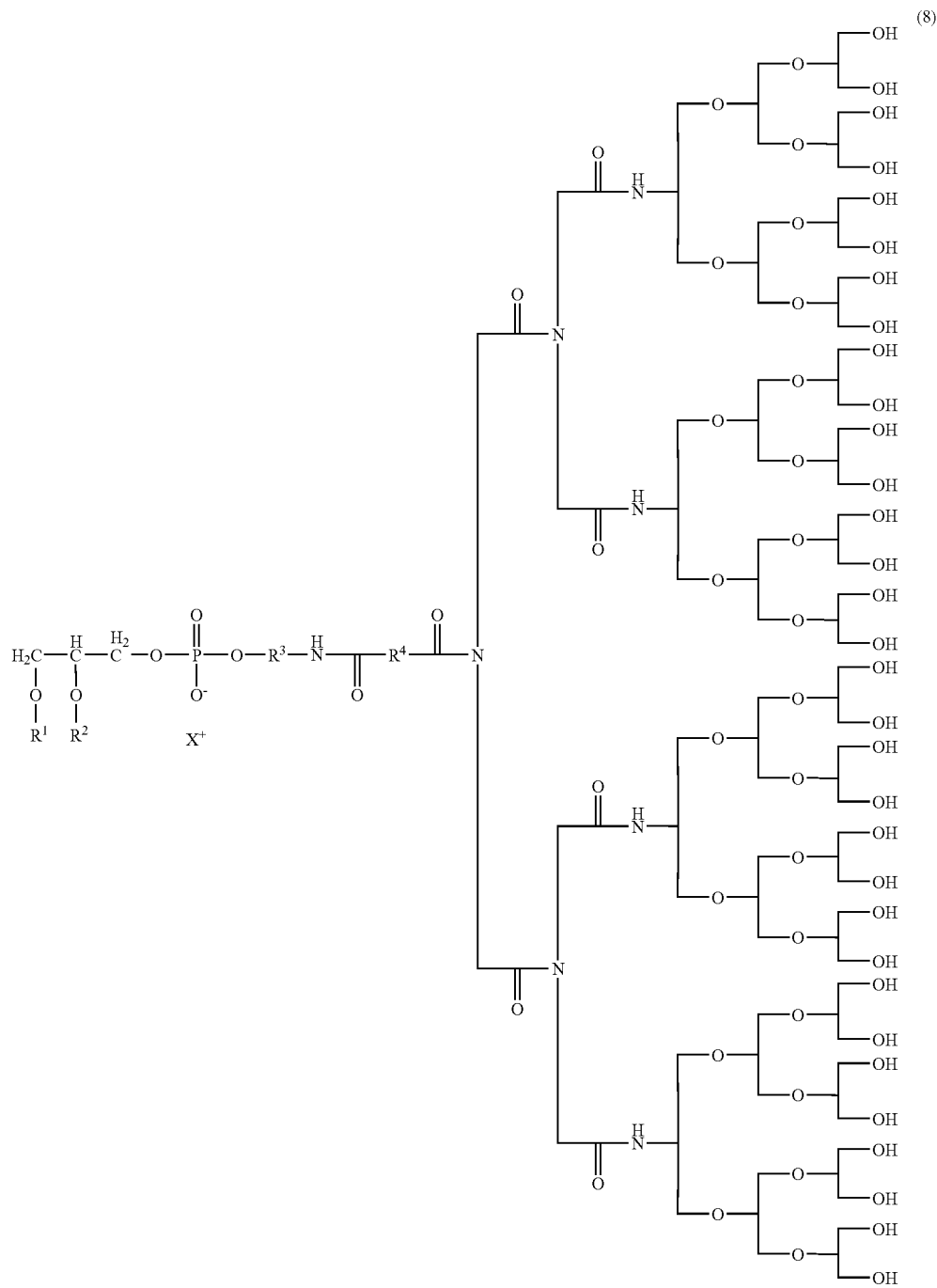

wherein X represents a hydrogen atom or an alkaline metal atom; $R^1$ and $R^2$, which may be the same or different, each represent a hydrogen atom, a saturated fatty acid residue or an unsaturated fatty acid residue, and at least one of $R^1$ and $R^2$ is the saturated fatty acid residue or the unsaturated fatty acid residue; and $R^3$ and $R^4$, which may be the same or different, each represent alkylene having 1 to 10 carbon atoms, or a salt thereof.

(20) A compound represented by the following formula (9):

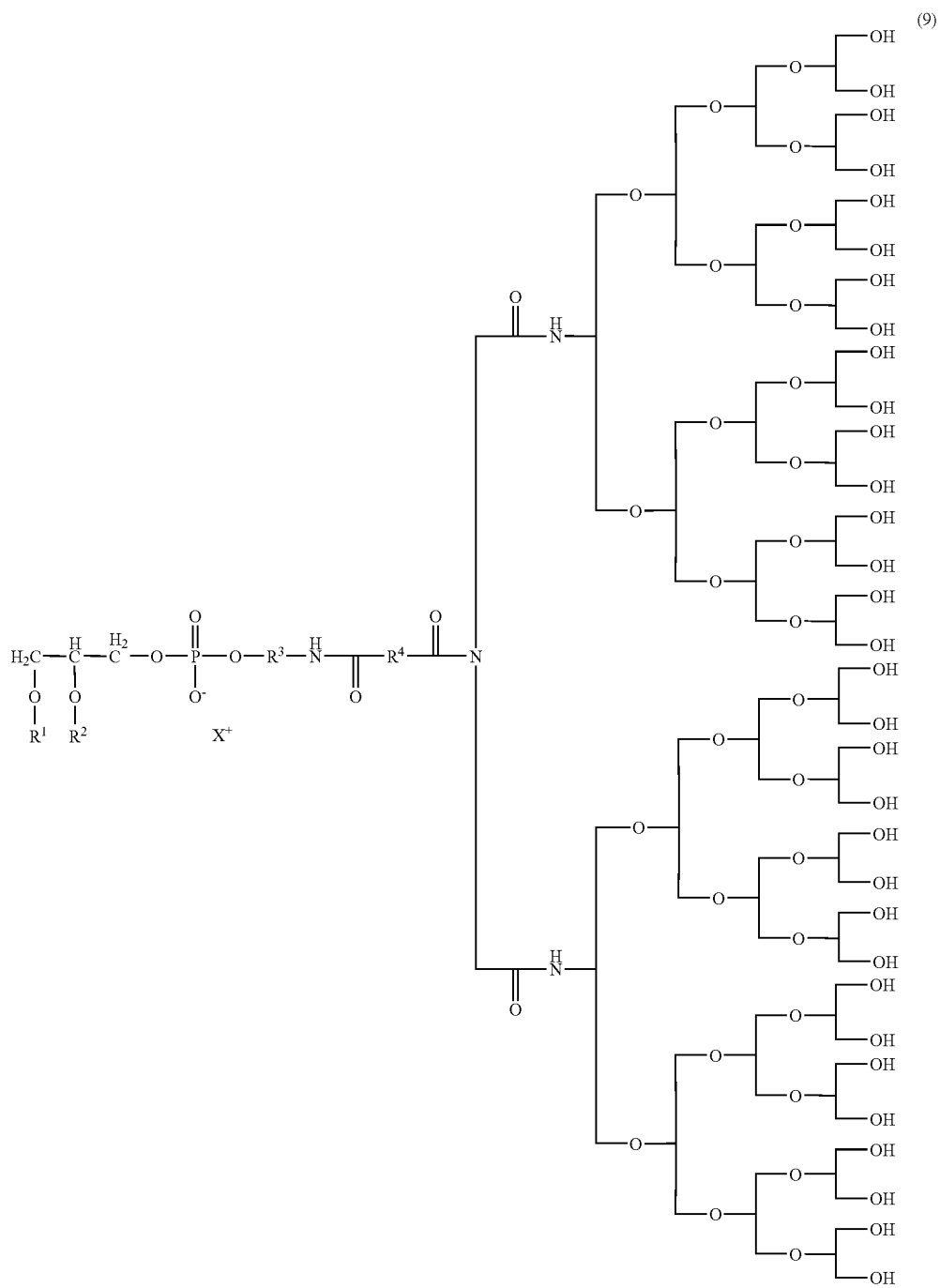

wherein X represents a hydrogen atom or an alkaline metal atom; $R^1$ and $R^2$, which may be the same or different, each represent a hydrogen atom, a saturated fatty acid residue or an unsaturated fatty acid residue, and at least one of $R^1$ and $R^2$ is the saturated fatty acid residue or the unsaturated fatty acid residue; and $R^3$ and $R^4$, which may be the same or different, each represent alkylene having 1 to 10 carbon atoms, or a salt thereof.

(21) A compound represented by the following formula (10):

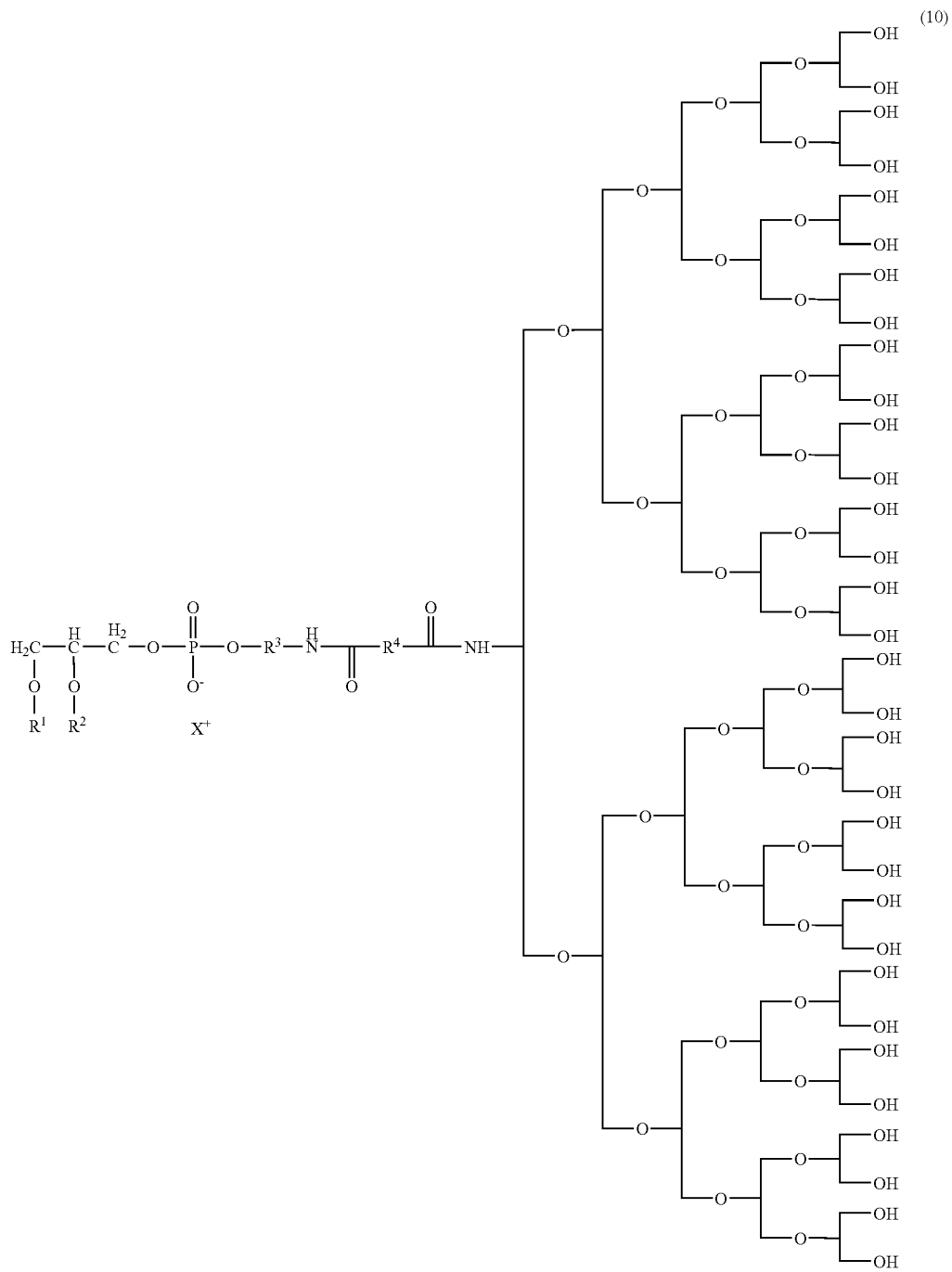

wherein X represents a hydrogen atom or an alkaline metal atom; $R^1$ and $R^2$, which may the same or different, each represent a hydrogen atom, a saturated fatty acid residue or an unsaturated fatty acid residue, and at least one of $R^1$ and $R^2$ is the saturated fatty acid residue or the unsaturated fatty acid residue; and $R^3$ and $R^4$, which may be the same or different, each represent alkylene having 1 to 10 carbon atoms, or a salt thereof.

(22) The compound according to any one of the above-described (13) to (21), wherein $R^3$ and $R^4$ are ethylene.

(23) A fine particle comprising a compound in which a substance to be modified, which is selected from the group consisting of an amphiphilic substance and a hydrophobic substance, is modified with a glycerol derivative which comprises a residue comprising a reactive group for the substance to be modified, which is selected from the group consisting of an amphiphilic substance and a hydrophobic substance or for a spacer capable of binding the substance to be modified, which is selected from the group consisting of an amphiphilic substance and a hydrophobic substance, to R-X, or a group capable of being transformed into the reactive group and one or more structure(s) represented by

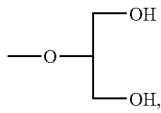

directly or via the spacer,
or a salt thereof.
(24) A fine particle comprising the compound according to any one of the above-described (1) to (22) or a salt thereof.
(25) The fine particle according to the above-described (23) or (24), wherein the fine particle is selected from the group consisting of a liposome, a fat emulsion, an emulsion, a micell and a fine particle crystal.
(26) A surface modifier of a fine particle, comprising a compound in which a substance to be modified, which is selected from the group consisting of an amphiphilic substance and a hydrophobic substance, is modified with a glycerol derivative which comprises a residue comprising a reactive group for the substance to be modified, which is selected from the group consisting of an amphiphilic substance and a hydrophobic substance or for a spacer capable of binding the substance to be modified, which is selected from the group consisting of an amphiphilic substance and a hydrophobic substance, to R-X, or a group capable of being transformed into the reactive group and one or more structure(s) represented by

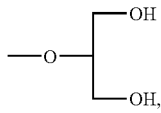

directly or via the spacer,
or a salt thereof.
(27) A surface modifier of a fine particle, comprising the compound according to any one of the above-described (1) to (22) or a salt thereof.
(28) The surface modifier according to the above-described (26) or (27), wherein the fine particle is selected from the group consisting of a liposome, a fat emulsion, an emulsion, a micell and a fine particle crystal.

BEST MODE FOR CARRYING OUT THE INVENTION

In the present invention,
(i) the glycerol derivative which comprises a residue containing a reactive group for a substance to be modified, which is selected from the group consisting of an amphiphilic substance and a hydrophobic substance or a group capable of being transformed into the reactive group and one or more structure(s) represented by

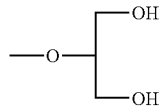

(hereinafter referred to as the glycerol derivative (I)) may be any one, so long as it has a structure which comprises the residue containing a reactive group for a substance to be modified, which is selected from the group consisting of an amphiphilic substance and a hydrophobic substance or a group capable of being transformed into the reactive group and one or more structure(s) represented by

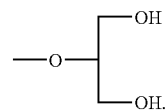

Examples include a glycerol derivative represented by the following formula (1) (hereinafter referred to as the glycerol derivative (1)):

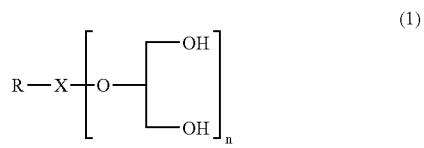

wherein R represents a residue comprising a reactive group for the substance to be modified, which is selected from the group consisting of an amphiphilic substance and a hydrophobic substance or a group capable of being transformed into the reactive group; n represents an integer of 3 or more; and X represents a residue capable of having the following structure by n in number

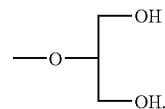

In formula (1), X is not particularly limited, so long as it is a group capable of binding to R and the following structure by n in number:

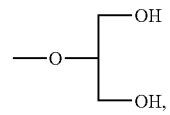

and it is preferred that it comprises at least one or more serially branched structure. Also, the serially branched structure means a structure in which at least one branched chain of branched chains which are branched into two or more, is further branched into two or more, and this branching is repeated. Particularly, the preferred structure is a structure in which each of the branched chains which are branched into two or more is further branched into two or more, and this branching is repeated. In addition, it is preferred that the number of respective branches is 2.

As the branched structure,

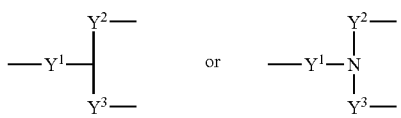

(wherein $Y^1$, $Y^2$ and $Y^3$ have the same meaning as described above, respectively) is preferred, and particularly, glycerol unit represented by

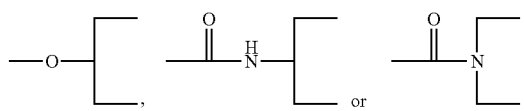

is more preferred. The number of these branched structures to be contained in formula (1) is not particularly limited, and is preferably one to (n–1), and when n is $2^m$, it is more preferably one to ($2^m$–2).

In addition, a glycerol derivative in which X in formula (1) comprises one to (n–1), or when n is $2^m$, one to ($2^m$–2), of a structure represented by

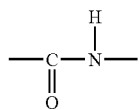

is also preferred.

Among the definitions of $Y^1$, $Y^2$ and $Y^3$, the alkylene includes, for example, straight-chain, branched or cyclic alkylene having 1 to 8 carbon atom(s), such as methylene, ethylene, propane-1,3-diyl, butane-1,4-diyl, pentane-1,5-diyl, hexane-1,6-diyl, heptane-1,7-diyl, octane-1,8-diyl, nonane-1,8-diyl, decane-1,9-diyl, cyclopropane-1,2-diyl, cyclobutane-1,2-diyl, cyclopentane-1,2-diyl, cyclohexane-1, 2-diyl, cyclooctane-1,2-diyl and the like.

The substituents of the substituted alkylene includes, for example, 1 to 3 substituent(s) which may be the same or different, such as a halogen atom, lower alkyl, an unsaturated hydrocarbon group, aryl, lower alkoxy, a hydroxyl group, oxo, carboxy, acyl, aroyl, amino, nitro, cyano and a heterocyclic group.

In this case, the halogen atom includes atoms of fluorine, chlorine, bromine and iodine. The lower alkyl and the lower alkyl moiety of the lower alkoxy include, for example, straight-chain or branched alkyl having 1 to 8 carbon atoms such as methyl, ethyl, n-propyl, isopropyl, n-butyl, isobutyl, sec-butyl, tert-butyl, pentyl, neopentyl, hexyl, heptyl and octyl. The unsaturated hydrocarbon group includes, for example, a straight-chain, branched or cyclic unsaturated hydrocarbon group having 1 to 8 carbon atom(s), for example, alkenyl and alkynyl such as vinyl, allyl, 1-propenyl, methacryl, 2-butenyl, 1-pentenyl, 2-hexenyl, 1,3-pentadienyl, 1,3-hexadienyl, cyclopentenyl, cyclopentadienyl, propargyl, pentynyl and the like. The aryl includes, for example, aryl having 6 to 14 carbon atoms, such as phenyl, naphthyl, anthranyl and the like. The acyl includes, for example, straight-chain, branched or cyclic acyl having 1 to 8 carbon atoms such as acetyl and propionyl. The aroyl includes, for example, benzoyl. The heterocyclic group includes, for example, a 3- to 8-membered heterocyclic group and the like containing at least one hetero atom of a nitrogen atom, an oxygen atom, a sulfur atom and the like, such as furyl, thienyl, pyrrolyl, pyridyl, oxazolyl, thiazolyl, imidazolyl, pyrimidinyl, triazinyl, indolyl, quinolyl, purinyl, benzoxazolyl, benzothiazolyl and benzimidazolyl.

The substituent in the substituted imino includes, for example, lower alkyl, aryl, aralkyl and the like.

The aralkyl includes, for example, aralkyl having 7 to 13 carbon atoms such as benzyl, phenetyl, benzhydryl and naphtylmethyl. The lower alkyl and the aryl have the same meaning as described above, respectively.

In formula (1), R is a residue comprising a reactive group for a substance to be modified, which is selected from the group consisting of an amphiphilic substance and a hydrophobic substance, or a group capable of being transformed into the reactive group. The reactive group as a partial structure of R may be any group, so long as it can react with carboxy, amino, a hydroxyl group, mercapto, formyl, a sulfuric acid residue (sulfonyl, sulfenyl, sulfinyl, etc.), a phosphoric acid residue (phosphono, phosphonoyl, phosphonato, hydroxyoxydophosphoryl, hydrohydroxyphosphoryl, phosphinoyl, hydroxyphosphoryl, phosphoryl, etc.), a phosphonic acid residue (dihydroxyphosphanyl, hydroxyoxydophosphanyl, hydroxyphosphanyl, hydoxyphosphanediyl, phosphinato, etc.) or the like or a partial structure thereof in the substance to be modified, which is selected from the group consisting of an amphiphilic substance and a hydrophobic substance.

Preferred examples of the reactive group for a substance to be modified, which is selected from the group consisting of an amphiphilic substance and a hydrophobic substance, include a carboxylic acid active ester residue, carbonate, maleimido, mercapto, formyl, tresyl, isocyanato, an acid anhydride residue, an acid halide residue, vinylsulfonyl, hydrazido, amino, halogen and the like.

Preferred examples of the group capable of being transformed into a reactive group for a substance to be modified, which is selected from the group consisting of an amphiphilic substance and a hydrophobic substance, include a hydroxyl group, carboxy, amino, mercapto, formyl, vinyl, phosphono, halogen and the like.

The carboxylic acid active ester of carboxylic acid active ester residue is ester having substituted or unsubstituted aryl, a substituted or unsubstituted heterocyclic group or the like. Examples include N-hydroxysuccinimide ester, p-nitrophenyl ester, thiophenyl ester, 2,3,5-trichlorophenyl ester, 2,4,6-trichlorophenyl ester, 2,4,5-trichlorophenyl ester, pentachlorophenyl ester, 2,4-dinitrophenyl ester, N-hydroxyphthalimido ester and the like.

The acid anhydride of the acid anhydride residue includes carboxylic anhydride and the like.

The acid halide residue includes carbonyl chloride, carbonyl bromide, carbonyl iodide, carbonyl fluoride and the like.

The moiety other than the reactive group or the group capable of being transformed into the reactive group in R is not particularly limited, so long as it is a group which does not inhibit the reactivity, and it may be an optional group. Examples include groups comprising one or two or more in optional combination, which may be the same or different, selected from the group consisting of a halogen atom, substituted or unsubstituted alkyl, a substituted or unsubstituted unsaturated hydrocarbon group, substituted or unsubstituted alkylene, substituted or unsubstituted aryl, substituted or unsubstituted alkoxy, a hydroxyl group, carbonyl, carboxy, substituted or unsubstituted acyl, substituted or unsubstituted aroyl, substituted or unsubstituted amino, substituted or unsubstituted imino, nitro, cyano, O, S, sulfinyl, sulfonyl, a substituted or unsubstituted heterocyclic group and the like. Among these, groups comprising one or two or more in optional combination, which may be the same or different, selected from the group consisting of substituted or unsubstituted alkylene, carbonyl, substituted or unsubstituted imino, O and S are preferred.

The alkyl moiety of the alkyl and the alkoxy of R includes, for example, straight-chain, branched or cyclic alkyl having 1 to 8 carbon atom(s), such as methyl, ethyl, n-propyl, isopropyl, n-butyl, isobutyl, sec-butyl, tert-butyl, pentyl, neopentyl, hexyl, heptyl, octyl, cyclopropyl, cyclobutyl, cyclopentyl, cyclohexyl, cycloheptyl, cyclooctyl and the like.

The halogen atom, the unsaturated hydrocarbon group, the alkylene, the aryl, the acyl, the aroyl and the heterocyclic group have the same meanings as the halogen atom, the unsaturated hydrocarbon group, the alkylene, the aryl, the acyl, the aroyl and the heterocyclic group, respectively, described above in the definitions of $Y^1$, $Y^2$ and $Y^3$.

The substituent(s) of the substituted alkyl, the substituted unsaturated hydrocarbon group, the substituted alkylene, the substituted aryl, the substituted alkoxy, substituted acyl, the substituted aroyl and the substituted heterocyclic group include, for example, 1 to 3 substituent(s) which may be the same or different, such as a halogen atom, alkyl, an unsaturated hydrocarbon group, aryl, alkoxy, a hydroxyl group, oxo, carboxy, acyl, aroyl, amino, nitro, cyano, a heterocyclic group and the like, and the halogen atom, the alkyl, the unsaturated hydrocarbon group, the aryl, the alkoxy, the acyl, the aroyl and the heterocyclic group have the same meaning as described above, respectively.

The substituent of the substituted imino includes, for example, alkyl, an unsaturated hydrocarbon group, aryl, alkoxy, acyl, aroyl, amino, a heterocyclic group and the like, the substituent of the substituted amino includes, for example, 1 or 2 substituent(s) which nay be the same or different, such as alkyl, an unsaturated hydrocarbon group, aryl, alkoxy, acyl, aroyl, amino, a heterocyclic group and the like, and the alkyl, the unsaturated hydrocarbon group, the aryl, the alkoxy, the acyl, the aroyl and the heterocyclic group have the same meaning as described above, respectively.

In formula (1), n is not particularly limited, so long as it is an integer of 3 or more, and is preferably $2^m$, wherein m has the same meaning as described above, and is more preferably from 4 to 1,024 ($2^2$ to $2^{16}$).

The molecular weight of the glycerol derivative (1) is not particularly limited, and the compound has preferably a molecular weight of 100 to 1,000,000, and more preferably 1,000 to 100,000.

Representative examples of the glycerol derivative (1) include compounds represented by the following formulae (1A), (1B), (1C), (1D), (1E), (1F), (1G) and the like.

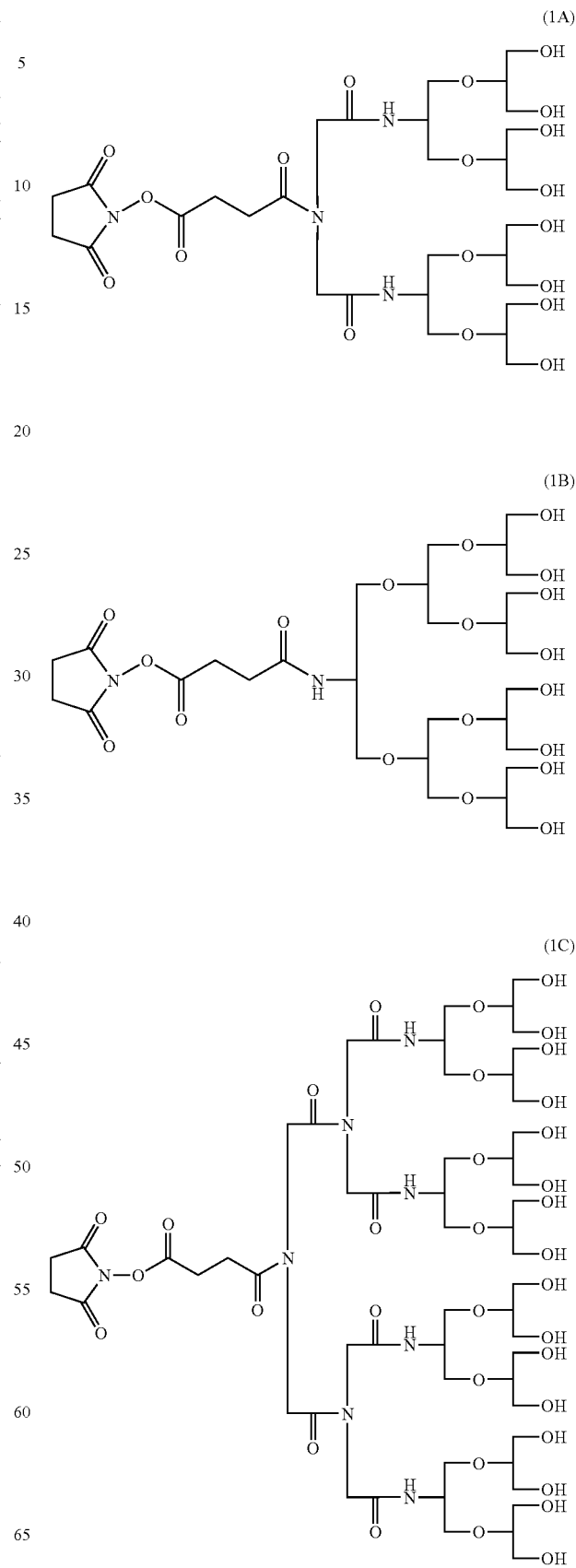

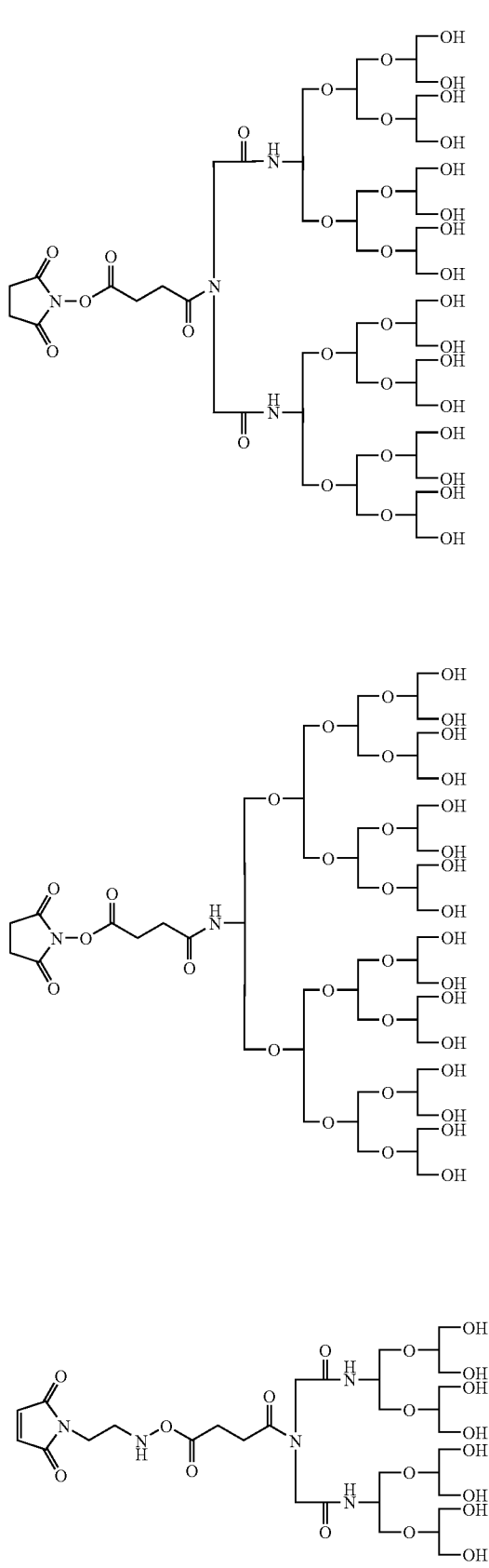
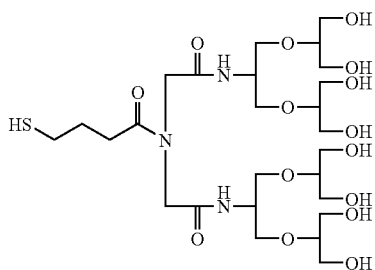
The glycerol derivative (1) can be produced by a combination of reactions known in usual organic synthesis methods [Edited by The Chemical Society of Japan, *Organic Synthesis*, I to IV, Experimental Chemistry Course, Vol. 19 to 22, edited by, Maruzen, (1992)] and the like. For example, the glycerol derivative (1) can be produced by the following usual production method.
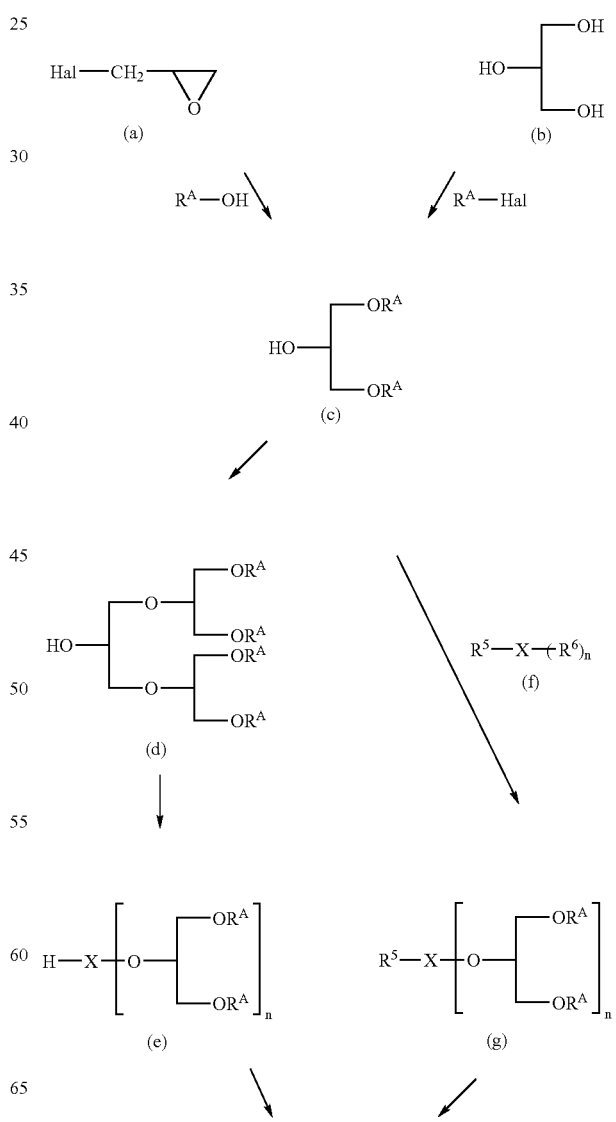

-continued

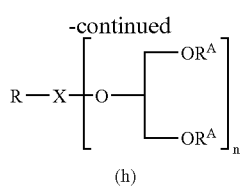

(h)

↓

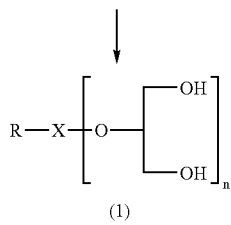

(1)

wherein R, X and n have the same meaning as described above, respectively; Hal represents a halogen atom; $R^4$ represents a group capable of being transformed into a hydrogen atom; $R^5$ represents a group capable of being transformed into R; and $R^6$ represents a group which can be substituted with

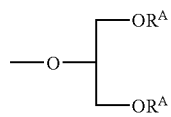

wherein $R^4$ has the same meaning as described above.

The halogen atom has the same meaning as described above.

The group which is transformed into a hydrogen atom includes, for example, substituted or unsubstituted lower alkyl, a substituted or unsubstituted alicyclic heterocycle group, substituted or unsubstituted silyl, substituted or unsubstituted acyl, substituted or unsubstituted aroyl and the like, and among these, benzyl and the like are preferred. Also, the group which is transformed into a hydrogen atom may be a group formed by combining two $R^4$s in one glycerol unit, such as substituted or unsubstituted alkylene, and among these, propane-2,2-diyl, phenylmethylene and the like are preferred.

The lower alkyl includes, for example, straight-chain or branched alkyl having 1 to 8 carbon atoms, such as methyl, ethyl, n-propyl, isopropyl, n-butyl, isobutyl, sec-butyl, tert-butyl, pentyl, neopentyl, hexyl, heptyl and octyl.

The alicyclic heterocycle group includes, for example, a 3- to 8-membered monocyclic alicyclic heterocycle group containing at least one atom selected from nitrogen, oxygen and sulfur atoms, a 3- to 8-membered rings-condensing bi- or tri-cyclic condensed alicyclic heterocycle group containing at least one atom selected from nitrogen, oxygen and sulfur atoms, and the like, such as tetrahydropyridinyl, tetrahydroquinolinyl, tetrahydroisoquinolinyl, tetrahydropyranyl, tetrahydrofuranyl, dihydrobenzofuranyl, pyrrolidinyl, piperidino, piperidinyl, perhydroazepinyl, perhydroazocinyl, morpholino, morpholinyl, thiomorpholino, thiomorpholinyl, piperazinyl, homopiperidino, homopiperazinyl, dioxolanyl, imidazolidinyl, imidazolinyl, pyrazolidinyl, indolinyl, isoindolinyl, 2-pyrrolinyl, 2-pyrrolidonyl, 3-pyrrolidonyl, 2-piperidonyl, 3-piperidonyl, 4-piperidonyl, perhydro-2-azepinonyl, perhydro-3-azepinonyl, perhydro-4-azepinonyl, 2-thiazolidonyl, 4-thiazolidonyl, 2-oxazolidonyl, 4-oxazolidonyl, phthalimido, glutarimido, hydantoinyl, thiazolidinedionyl and oxazolidinedionyl.

The acyl and aroyl have the same meanings as described above, respectively.

The alkylene includes, for example, methylene, ethylene, propane-1,3-diyl, butane-1,4-diyl, pentane-1,5-diyl, and hexane-1,6-diyl.

The substituent of the substituted lower alkyl, the substituted alicyclic heterocycle group, the substituted silyl, the substituted acyl and the substituted aroyl includes, for example, 1 to 3 substituent(s) which may be the same or different, such as lower alkyl, lower alkoxy, lower alkoxy-lower alkoxy and aralkyloxy. The substituent of the substituted lower alkyl includes, for example, 1 or 2 substituent(s) of aryl, and the aryl includes, for example, phenyl, naphtyl and the like. The substituent of the substituted aryl includes, for example, 1 to 3 substituent(s), such as lower alkyl, lower alkoxy, lower alkoxy-lower alkoxy and aralkyloxy. The lower alkyl and the lower alkyl moiety of the lower alkoxy and the lower alkoxy-lower alkoxy have the same meanings as the above lower alkyl, the aryl moiety of the aralkyloxy has the same meaning as the above aryl, and the alkylene moiety of the aralkyloxy includes, for example, methylene, ethylene, propane-1,3-diyl, butane-1,4-diyl, pentane-1,5-diyl, hexane-1,6-diyl and the like.

The substituent of the substituted alkylene includes, for example, 1 to 3 substituent(s) which may be the same or different, such as lower alkyl, aryl and lower alkoxy. The lower alkyl and the lower alkyl moiety of the lower alkoxy have the same meanings as the above lower alkyl, and the aryl has the same meaning as the above aryl.

The group capable of being transformed into R is not particularly limited, so long as it is a group capable of being transformed into R, and examples include those described in the definition of the group capable of being transformed into a hydrogen atom.

The group which can be substituted with

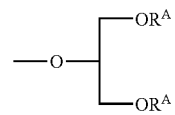

(wherein $R^4$ has the same meaning as described above) is not particularly limited, so long as it is a group which can be substituted with

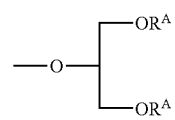

(wherein $R^4$ has the same meaning as described above), and examples include a hydrogen atom, a halogen atom, a hydroxyl group, alkoxy, alkanoyloxy and the like, wherein the halogen atom has the same meaning as described above, and the alkyl moiety of the alkoxy and the alkanoyloxy has the same meaning as the above-described alkyl.

Compound (c) can be obtained in accordance with the methods described in *J. Org. Chem*, 57, 435 (1992), *J. Med. Chem*, 38 (10), 1673 (1995) and the like by using epihalohydrin (Compound (a)) such as epichlorohydrin, epibromohydrin, epifluorohydrin or the like and $R^4$—OH (wherein $R^4$ has the same meaning as described above). Also, Compound (c) can be obtained by allowing 1 mole of glycerol (compound (b)) to react with 1 to 10 mole(s) of $R^A$-Hal (wherein $R^A$ and Hal have the same meaning as described above, respectively) in the presence of an appropriate base and then purifying the product, or by allowing it to react with 2-methyl-1-butene in the presence of a catalytic amount of $BF_3 \cdot O(C_2H_5)_2$ [*Tetrahedron Lett,* 29, 2951 (1988)], thereby selectively protecting a hydroxyl group of the primary alcohol, or in accordance with the methods described in *Tetrahedron Lett,* 41, 6411 (2000), *J. Org. Chem,* 54, 1346 (1989), *Can. J. Chem,* 62, 241 (1984) and the like. In addition, Compound (c) can be obtained by protecting a hydroxyl group of the primary alcohol of compound (b) in accordance, for example, with the protective group introducing method described in *Protective Groups in Organic Synthesis*, third edition, edited by T. W. Greene, John Wiley & Sons, Inc. (1999) or the like.

As the $R^A$—OH to be allowed to react with Compound (a), for example, various alcohols such as methanol, ethanol, propanol, tert-butyl alcohol, benzyl alcohol and the like can be used. Also, as the $R^A$ of $R^A$-Hal to be allowed to react with Compound (b), it is possible to use a residue which can be removed, such as benzyl, methyl, ethyl, propyl, tert-butyl, methoxymethyl, methoxyethoxymethyl, tetrahydropyranyl, tetrahydrofuranyl, triphenylmethyl, benzyloxymethyl, triethylsilyl or the like. Commercially available products can be used as Compounds (a) and (b), and Compound (c) can be synthesized in accordance with the above-described method or can be obtained as a commercially available product.

Next, Compound (d) is obtained by further reacting Compound (c) obtained by the above-described step with Compound (a), or by reacting Compound (b) with

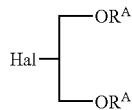

(wherein Hal and $R^A$ has the same meaning as described above, respectively).

By repeating this reaction step, Compound (e) wherein X comprises a serially branched structure, and n Compound (c) residues are bound to X, can be obtained.

Also, Compound (e) having n Compound (c) residues bound to X having a series branch structure can be obtained by combining the above reaction steps with the following reaction steps and/or repeating them.

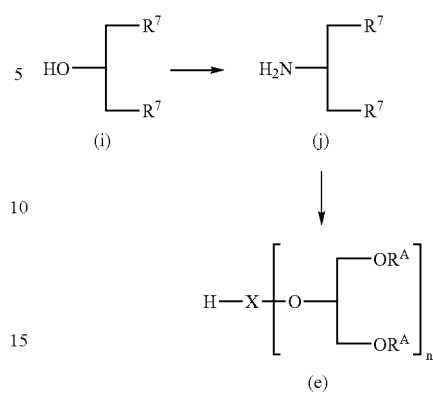

wherein X, $R^A$ and n have the same meanings as described above, respectively; and $R^7$ represents

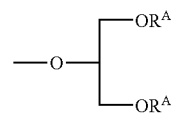

(wherein $R^A$ has the same meaning as described above) or

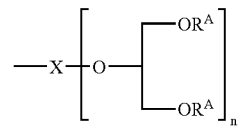

(wherein X, $R^A$ and n have the same meanings as described above, respectively).

Compound (j) can be obtained by a method described in *J. Med. Chem,* 38 1673 (1995) and the like, or by combining reactions known in usual organic synthesis methods [Edited by The Chemical Society of Japan, *Organic Synthesis*, I to IV, Experimental Chemistry Course, 4th Ed, Vol. 19 to 22, edited by, Maruzen, (1992), and the like].

Also, Compound (e) having n compound (c) residues bound to X having a series branch structure can be obtained by combining the above reaction steps with the following reaction steps and/or repeating them.

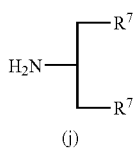

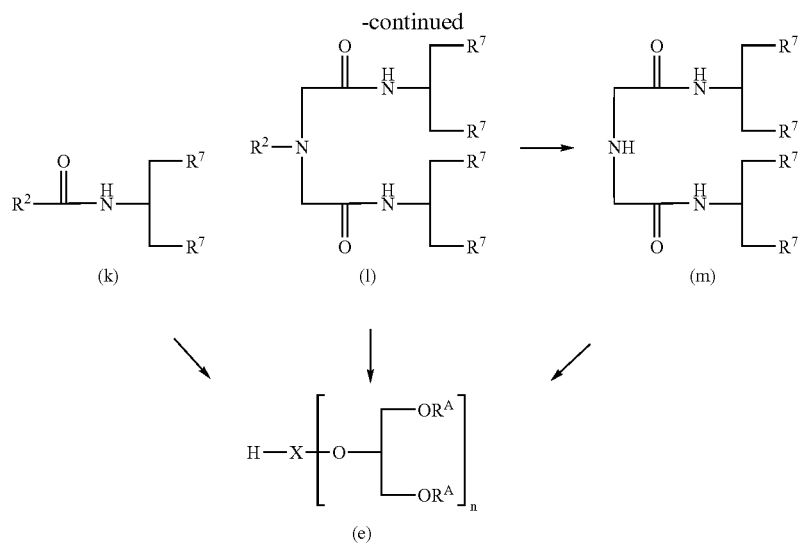

(k) (l) (m)

(e)

wherein X, $R^A$ and n have the same meanings as described above, respectively; $R^7$ represents

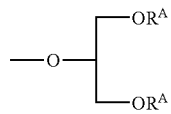

(wherein $R^A$ has the same meaning as described above) or

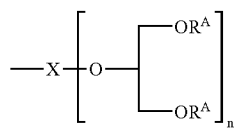

wherein X, $R^A$ and n have the same meanings as described above, respectively; and $R^8$ represents a group which can be substituted with a hydrogen atom.

Compound (k) can be obtained by reactions known in usual organic synthesis methods [Edited by The Chemical Society of Japan, *Organic Synthesis*, I to IV, Experimental Chemistry Course, 4th Ed, Maruzen, Vol. 19 to 22 (1992) and the like].

Compound (l) can be obtained by dimerizing two amines using a linker (a crosslinking agent) having a $HO_2C$—$CH_2$—$NR^8$—$CH_2$—$CO_2H$ skeleton ($R^8$ represents a group which can be substituted with a hydrogen atom) (Toth, G. K., Botond, P., *Synthesis*, p. 361 (1992)), and then Compound (m) can be obtained by subjecting Compound (1) to amine deprotection reaction described in T. W. Greene, *Protective Groups in Organic Synthesis*, Third Edition, John Wiley & Sons Inc. (1999), and the like.

Compound (h) can be obtained by binding the residue R containing a reactive group or a group capable of being transformed into the reactive group to the X-terminal hydroxyl group existing in Compound (e), by using a general organic synthesis reaction, or by directly being transformed the hydroxyl group into a reactive residue.

On the other hand, Compound (g) can be obtained by reacting Compound (f) with Compound (c) synthesized in the similar manner as described above. The method for obtaining Compound (g) by reacting Compound (f) with Compound (c) includes a substitution reaction of the $R^6$ moiety of Compound (f) with Compound (c), a combination of reactions known in usual organic synthesis methods [Edited by The Chemical Society of Japan, *Organic Synthesis*, I to IV, Experimental Chemistry Course, 4th Ed, Maruzen, Vol. 19 to 22 (1992) and the like] and the like. Compound (h) can be obtained by converting $R^2$ of Compound (g) into the residue R comprising a reactive group or a group capable of being transformed into the reactive group, by using a general organic synthesis reaction. A commercially available compound having a known structure can be used as Compound (f), or Compound (f) can be prepared by combining the reactions known in usual organic synthesis methods [Edited by The Chemical Society of Japan, *Organic Synthesis*, I to IV, Experimental Chemistry Course, 4th Ed, Maruzen, Vol. 19 to 22 (1992) and the like].

The glycerol derivative (1) is obtained by subjecting Compound (h) to a protecting group removing reaction generally used in the organic synthesis reactions [e.g., *Protective Groups in Organic Synthesis*, third edition, edited by T. W. Greene, John Wiley & Sons, Inc. (1999) and the like] to thereby remove $R^A$ and replace it with a hydrogen atom.

On the contrary to this, in formula (I), it is possible to produce the glycerol derivative (1) by elongating the glycerol unit from the —OH terminus, in the opposite direction of X.

Each reaction step is carried out in an appropriate solvent, preferably a solvent optionally selected from dichloromethane, chloroform, N,N-dimethylformamide, dimethyl sulfoxide, toluene, tetrahydrofuran, acetonitrile, methanol, ethanol, pyridine, water and mixed solvents thereof at a temperature of –20 to 150° C. for 1 hour to several days.

Each of the compounds obtained by respective steps can be used in the subsequent step with the purity as such, or after purifying it to an optional purity by general purification methods such as recrystallization, solvent extraction, silica gel chromatography, reverse phase chromatography, normal phase chromatography and the like.

(ii) The amphiphilic substance includes, for example, lipids such as phospholipid, glyceroglycolipid, sphingoglycolipid, sphingoids, sterols, cationic lipid and anionic lipid; surfactants such as polyhydric alcohol ester nonionic surfactant, anionic surfactant, cationic surfactant and ampholytic surfactant; and the like.

Examples of the phospholipid include natural or synthesized phospholipid, for example, glycerophospholipid such as phosphatidylcholine (e.g., soy phosphatidylcholine, yolk phosphatidylcholine, distearoylphosphatidylcholine (DSPC), dipalmitoylphosphatidylcholine (DPPC), dimyristoylphosphatidylcholine (DMPC), dioleoylphosphatidylcholine (DOPC), etc.), phosphatidylethanolamine (e.g, distearoylphosphatidylethanolamine (DSPE), dipalmitoylphosphatidylethanolamine (DPPE), dioleoylphosphatidylethanolamine (DOPE), etc.), phosphatidylserine, phosphatidic acid, phosphatidylglycerol, phosphatidylinositol and lysophosphatidylcholine; sphingophospholipid such as sphingomyelin, ceramide phosphoethanolamine, ceramide phosphoglycerol and ceramide phosphoglycerophosphoric acid; glycerophosphonolipid; sphingophosphonolipid; natural lecithin (e.g, yolk lecithin, soy lecithin, etc.); hydrogenated phospholipid (e.g, hydrogenated phosphatidylcholine (HSPC), etc.); and the like.

The glyceroglycolipid includes, for example, sulfoxyribosyl glyceride, diglycosyl diglyceride, digalactosyl diglyceride, galactosyl diglyceride, glycosyl diglyceride and the like.

The sphingoglycolipid includes, for example, galactosyl cerebroside, lactosyl cerebroside, ganglioside and the like.

The sphingoids include, for example, sphingan, icosasphingan, sphingosine, derivatives thereof and the like. The derivatives include, for example, those obtained by converting —$NH_2$ of sphingan, icosasphingan, sphingosine or the like to —$NHCO(CH_2)_xCH_3$ (wherein x is an integer of 0 to 18, preferably 6, 12 or 18).

The sterols include cholesterol, dihydrocholesterol, lanosterol, β-sitosterol, campesterol, stigmasterol, brassicasterol, ergocasterol, fucosterol and the like.

The cationic lipid includes, for example, 1,2-dioleoyl-3-trimethylammonium propane (DOTAP), N-[1-(2,3-dioleyloxy)propyl]-N,N,N-trimethylammonium chrolide (DOTMA), 2,3-dioleyloxy-N-[2-(sperminecarboxyamido) ethyl]-N,N-dimethyl-1-propanaminium trifluoroacetate (DOSPA), N-[2,3-(ditetradecyloxy)propyl]-N,N-dimethyl-N-hydroxyethylammonium bromide (DMRIE), N-[1-(2,3-dioleyloxy)propyl]-N,N-dimethyl-N-hydroxyethylammonium bromide (DORIE) 3β-[N-(N',N'-dimethylaminoethyl) carbamoyl]cholesterol (DC-Chol) and the like.

The anionic lipid includes, for example, phosphatidylserine, phosphatidylglycerol, phosphatidylinositol and the like.

The polyhydric alcohol ester nonionic surfactant includes, for example, fatty acid monoglyceride, fatty acid diglyceride, fatty acid triglyceride, sorbitan ester of fatty acid, polyoxysorbitan ester of fatty acid, sucrose ester of fatty acid and the like. Specific examples include octyl glucoside, digitonin, decanoyl-N-methylglucamide and the like.

The anionic surfactant includes, for example, acyl sarcosine, sodium alkylsulfate, an alkylbenzenesulfonate salt, a sodium salt of fatty acid having 7 to 22 carbon atoms and the like. Specific examples include sodium dodecylsulfate, sodium laurylsulfate, sodium cholate, sodium deoxycholate, sodium taurodeoxycholate and the like.

The cationic surfactant includes, for example, an alkylamine salt, an acylamine salt, a quaternary ammonium salt, amine derivatives and the like. Specific examples include a primary amine salt, an acylaminoethyldiethylamine salt, an N-alkylpolyalkylpolyamine salt, fatty acid polyethylene polyamide, cetyltrimethylammonium bromide, dodecyltrimethylammonium bromide, alkylpolyoxyethyleneamine, N-alkylaminopropylamine, triethanolamine ester of fatty acid and the like.

The ampholytic surfactant includes, for example, 3-[(3-cholamidopropyl)dimethylammonio]-1-propanesulfonic acid, N-tetradecyl-N,N-dimethyl-3-ammonio-1-propanesulfonic acid and the like.

The hydrophobic substance includes, for example, an oil substance, a hydrophobic polymer and the like.

The oil substance includes, for example, liquid paraffin, vegetable oil (soy oils, etc.), ester of fatty acid having 12 to 30 carbon atoms, castor oil, castor oil derivatives (polyoxyethylene castor oil, etc.), lanolin, lanolin derivatives, silicon and the like.

The hydrophobic polymer includes, for example, polyaspartic acids, poly(β-benzyl aspartate), poly(γ-benzyl glutamate), poly(β-alkyl aspartate), polylactide, poly(ε-caprolactone), poly(δ-valerolactone), poly(γ-butyrolactone), poly(β-benzyl aspartate-co-aspartic acid), poly(γ-benzyl glutamate-co-glutaminic acid), poly(α-amino acid) and the like.

(iii) The compound of the present invention (hereinafter referred to as Compound (1)) may be any one, so long as the amphiphilic or hydrophobic substance (ii) is modified with the glycerol derivative (1) directly or via the spacer. Specific examples of Compound (1) include the compounds represented by formulae (2) to (10) (hereinafter referred to as Compounds (2) to (19), respectively).

In definition of each group in formulae (2) to (10), the saturated or unsaturated fatty acid residue includes, for example, an acyl moiety of a straight-chain or branched saturated or unsaturated fatty acid having 12 to 30 carbon atoms, and specific examples include dodecanoyl, tridecanoyl, tetradecanoyl, pentadecanoyl, hexadecanoyl, heptadecanoyl, octadecanoyl, nonadecanoyl, eicosanoyl, henicosanoyl, docosanoyl, tricosanoyl, tetracosanoyl, hexacosanoyl, triacontanoyl, 4-dodecenoyl, 9-hexadecenoyl, 9-octadecenoyl, 11-eicosenoyl, 13-docosenoyl, 15-tetracosenoyl, 9,12-octadecadienoyl, 11,14-eicosadienoyl, 9,12,15-octadecatrienoyl, 11,14,17-eicosatrienoyl, 4,8,12,16-eicosatetraenoyl, 4,8,12,15,19-docosapentaenoyl, 2-decanylhexadecanoyl, 2-tetradecylhexadecanoyl, 2-tetradecylhexadecenoyl, 2-tetradecenylhexadecanoyl and the like.

The alkaline metal atom includes, for example, sodium, potassium and the like.

The alkylene group having 1 to 10 carbon atoms includes, for example, methylene, ethylene, propane-1,2-diyl, propane-2,2-diyl, propane-1,3-diyl, butane-1,4-diyl, pentane-1,5-diyl, hexane-1,6-diyl, heptane-1,7-diyl, octane-1,8-diyl, nonane-1,8-diyl, decane-1,9-diyl and the like.

The compound of the present invention further includes, for example, those in which a PEG moiety of a triton surfactant is modified with the glycerol derivative (1) or a PEG moiety of a Tween surfactant is modified with the glycerol derivative (1) in addition to the above examples. Furthermore, the compound of the present invention includes those in which a PEG moiety of each of a mixture of polyoxyethylene alkyl ether and stearyl alcohol, polyoxyethylene alkyl ether, polyoxyethylene octylphenyl ether, polyoxyethylene oleyl amine, polyoxyethylene oleyl ether, polyoxyethylene oleyl ether phosphate diethanolamine, sodium polyoxyethylene oleyl ether phosphate, polyoxyethylene hydrogenated castor oil, polyoxyethylene distyrylphenyl ether, polyoxyethylene stearyl ether, polyoxyethylene stearyl ether phosphate, polyoxyethylene cetyl ether, a mixture of polyoxyethylene cetyl ether and distearate polyethylene glycol, sodium polyoxyethylene cetyl ether phosphate, polyoxyethylene cetostearyl ether, polyoxyethylene sorbitan monolaurate, polyoxyethylene sorbit beeswax, polyoxyethylene polycyclic phenyl ether ammonium sulfate, polyoxyethylene nonylphenyl ether, a mixture of polyoxyethylene nonylphenyl ether and calcium alkylbenzenesulfonate, polyoxyethylene castor oil, polyoxyethylene behenyl ether, polyoxyethylene polyoxypropylene glycol, polyoxyethylene polyoxypropylene cetyl ether, polyoxyethylene coconut oil fatty acid glyceryl, polyoxyethylene lanolin, polyoxyethylene lanolin alcohol ether and the like is modified with the glycerol derivative (1).

The salt of the compound includes, for example, hydrochloride, hydrobromide, nitrate, sulfate, phosphate, a sodium salt, a potassium salt, a magnesium salt, a calcium salt, an ammonium salt, a tetramethylammonium salt, a morpholine addition salt, a piperidine addition salt and the like.

(iv) The modification of the amphiphilic substance or the hydrophobic substance with the glycerol derivative (1) can be carried out, for example, by binding the reactive group in the glycerol derivative (1) to carboxy, amino, a hydroxyl group, mercapto, formyl, a sulfuric acid residue (sulfonyl, sulfenyl, sulfinyl, etc.), a phosphoric acid residue (phosphono, phosphonoyl, phosphonato, hydroxyoxidophosphoryl, hydrohydroxyphosphoryl, phosphinoyl, hydroxyphosphoryl, phosphoryl, etc.), a phosphonic acid residue (dihydroxyphosphanyl, hydroxyoxidophosphanyl, hydroxyphosphanyl, hydroxyphosphanediyl, phosphinato, etc.) or a moiety thereof in the structure of the amphiphilic substance or hydrophobic substance directly or via the spacer.

The spacer may be any one, so long as it can bind the glycerol derivative (1) to the binding site in the structure of each of the amphiphilic substance and the hydrophobic substance, and examples include a straight-chain linking group of one, or two or more in any combination, which may be the same or different, selected from the group consisting substituted or unsubstituted alkylene (in which the alkylene and the substituent of the substituted alkylene have the same meanings as those, respectively, described in the definitions of $Y^1$, $Y^2$ and $Y^3$), carbonyl, substituted or unsubstituted imino (in which the substituent of the substituted imino has the same meaning as described above), O and S; and the like.

The spacer is bound, for example, via an ether bond, amide bond, thioether bond, ester bond or the like to carboxy, amino, a hydroxyl group, mercapto, formyl, a sulfuric acid residue (sulfonyl, sulfenyl, sulfinyl, etc.), a phosphoric acid residue (phosphono, phosphonoyl, phosphonato, hydroxyoxidophosphoryl, hydrohydroxyphosphoryl, phosphinoyl, hydroxyphosphoryl, phosphoryl, etc.), a phosphonic acid residue (dihydroxyphosphanyl, hydroxyoxidophosphanyl, hydroxyphosphanyl, hydroxyphosphanediyl, phosphinato, etc.), a partial structure thereof or the like in the amphiphilic substance or the hydrophobic substance. The bond can be formed by usual peptide synthesis methods [Nobuo Izumiya, Tetsuo Kato, Haruhiko Aoyagi and Michinori Waki, *Basis and Experiment of Peptide Synthesis*, Maruzen (1985), etc.] and the like.

In this case, the spacer is preferably introduced to the amphiphilic substance or the hydrophobic substance beforehand; however, the spacer can be bound to the glycerol derivative (1) as the modifier and then the spacer bound to the glycerol derivative (1) can be bound to the amphiphilic substance or the hydrophobic substance in the above manner.

Each compound obtained in each step may be used in the next step without purification or after purification by usual purification methods such as recrystallization, solvent extraction, silica gel chromatography, reversed phase chromatography and normal phase chromatography.

Also, the glycerol derivative (1) is used as a chemical modifier for the amphiphilic substance or the hydrophobic substance, and a precursor of a glycerol derivative in which a part or the whole of hydroxyl groups at the terminals of the glycerol derivative (1) are protected —$OR^4$ (in which $R^4$ has the same meaning as described above) can used as a chemical modifier in the reaction with the amphiphilic substance or the hydrophobic substance. In this case, after the amphiphilic or hydrophobic substance is modified with the precursor, objective Compound (1) can be obtained by carrying out removal reaction of the protective group in the same manner as in the above-described Compound (h).

In the compound of the present invention, the substance to be modified, selected from the amphiphilic substance and the hydrophobic substance is modified with one or a combination of two or more which may be the same or different, of glycerol derivatives (1), preferably modified with one or a combination of two or more which are the same, of the glycerol derivatives (1).

The compound of the present invention can be used as a surface modifier for producing a drug carrier (for example, a fine particle capable of holding or encapsulating a drug or the like). Also, the compound of the present invention can be used as a component of a drug carrier, and has an effect of improving the productivity of the drug carrier.

(v) The fine particle of the present invention comprises the compound in which the amphiphilic substance or the hydrophobic substance described in the above (ii) is modified with the glycerol derivative (I) directly or via the spacer (hereinafter referred to as Compound (I)) or the salt thereof, and Compounds (I) to be contained may be a combination of different kinds. Compound (I) can be produced in the same manner as the above-described preparation of Compound (1).

The fine particle may further comprise a lipid and/or a surfactant, and the embodiments of the fine particle are not limited. The fine particles preferably have an average particle diameter of 1 nm to 1000 µm, and include liposomes [multilayer liposomes such as MLV (multilamellar vesicles); single membrane liposomes such as LUV (large unilamellar vesicles) and SUV (small unilamellar vesicles); etc.], fat emulsions (microcapsules, microspheres, etc.), emulsions (lipid emulsions, microemulsions, etc.), micells (polymer micells, lipid micells, etc.), fine particle crystals (platy, columnar, needle-like, fibrous, spherical, cubic and prismatic crystals, etc.) and the like. The fine particle is preferably the liposome.

The lipid contained in the fine particle includes, for example, phospholipid, glyceroglycolipid, sphingoglycolipid, sphingoids, sterols, cationic lipid, anionic lipid, those which is bound to polyethylene glycol via an ether bond (those which is polyethyleneglycolated) and the like. Among these, the lipid preferably having a phase transition temperature higher than living body temperature (35 to 37° C.) is preferred, and phospholipid and/or polyethyleneglycolated phospholipid is/are more preferred.

The surfactant contained in the fine particle includes, for example, a polyhydric alcohol ester nonionic surfactant, an anionic surfactant, a cationic surfactant, an ampholytic surfactant, those bound to polyethylene glycol thereto via an ether bond (those which is polyethyleneglycolated) and the like.

The phospholipid, the glyceroglycolipid, the sphingoglycolipid, the sphingoids, the sterols, the cationic lipid, the anionic lipid, the polyhydric alcohol ester nonionic surfactant, the anionic surfactant, the cationic surfactant and the ampholytic surfactant include those described in the above (ii), respectively, and they may be used alone or in combination. When they are used in combination, for example, in the case of the liposome and the fat emulsion, the combination includes, for example, lipids comprising at least two selected from the group consisting of hydrogenated soy phosphatidylcholine, polyethyleneglycolated phospholipid and cholesterol, lipids comprising at least two selected from the group consisting of DSPC, polyethyleneglycolated phospholipid and cholesterol, lipids comprising yolk phosphatidylcholine and DOTAP, lipids comprising yolk phosphatidylcholine, DOTAP and polyethyleneglycolated phospholipid, lipids comprising yolk phosphatidylcholine, DOTAP, cholesterol and polyethyleneglycolated phospholipid, and the like. In the case of the emulsion and the micell, polyoxysorbitan ester of fatty acid, sorbitan ester of fatty acid, a sodium salt of fatty acid, polyethylene hydrogenated castor oil and the like are preferably used alone or in combination.

Also, the fine particle of the present invention may comprise additives such as an isotonizing agent, a membrane stabilizer, an antioxidant and a charged substance, if necessary. The isotonizing agent includes, for example, glycerin, glucose, sodium chrolide and the like. The membrane stabilizer includes, for example, sterols such as cholesterol, and the like. The antioxidant includes, for example, tocopherol, citric acid, ascorbic acid, cysteine, ethylenediaminetetraacetic acid (EDTA) and the like. The charged substance includes, for example, stearylamine, dicetyl phosphate, ganglioside, cation lipid such as DOTMA [*Proc. Natl. Acad. Sci. U.S.A.*, 84, 7413-7417 (1987)], dioctadecylamidoglycylspermine (DOGS) [*Proc. Natl. Acad. Sci. U.S.A.*, 86, 6982-6986 (1989)], DMRIE, DORIE [Methods, 5, 67-75 (1993)] and DC-Chol [*Biochem. Biophys. Res. Comun.*, 179, 280-285 (1991)], and the like.

The fine particle of the present invention can be prepared by usual known methods, and can be prepared, for example, by a method in which (1) the above-described lipid and/or surfactant and the compound of the present invention, if necessary, together with the above-described additive are dissolved in a solvent of ethanol, ether or the like, the solvent is evaporated if necessary, and a solution for suspension is added to obtain dispersion, emulsion or suspension, or (2) they are directly dispersed, emulsified or suspended in a solution for suspension. Also, the fine particle of the present invention can be obtained by preparing a fine particle material to be modified according to a usual known method, adding the compound of the present invention, for example, as a powder, an aqueous solution or an ethanol solution, to the prepared liquid (dispersion, emulsion or suspension) of the fine particle to be modified, and allowing the resulting mixture to stand for a certain period, preferably heating the mixture at the phase transition temperature of the membrane or higher and allowing the mixture to stand for cooling.

The solution for suspension includes, for example, distilled water, an acidic aqueous solution (aqueous solution of hydrochloric acid, sulfuric acid, acetic acid, etc.), an alkali aqueous solution (aqueous solution of sodium hydroxide, calcium hydroxide, sodium hydrogen carbonate, etc.), buffer (phosphoric acid buffer, etc.), saline, amino acid infusion solution and the like.

The fine particle of the present invention is preferably a fine particle with one or more structure(s) represented by

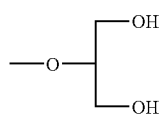

in Compound (1) extending outward from the fine particle surface (hereinafter referred to as the glycerol derivative-modified fine particle; in the case of using, for example, the liposome as the fine particle, it is referred to as the glycerol derivative-modified liposome). The glycerol derivative-modified fine particle can be prepared by using the compound of the present invention as a surface modifier in the preparation of the fine particle of the present invention. The use of the compound of the present invention as a surface modifier means that the compound of the present invention is used in the preparation of the fine particle of the present invention such that the compound is contained in the outermost portion of the fine particle.

Specifically the fine particle of the present invention, such as liposome, can be produced by a known preparation method. The preparation method includes, for example, a liposome preparation method by Bangham, et al. [*J. Mol. Biol.*, 13, 238 (1965)], an ethanol injection method [*J. Mol. Biol*, 66, 621 (1975)], a French press methods [*FEBS Lett.*, 99, 210 (1979)], a freezing and thawing method [*Arch. Biochem. Biophys.*, 212, 186 (1981)], a reversed-phase evaporation method [*Proc. Natl. Acad. Sci. U.S.A.*, 75, 4194 (1978)], a pH gradient method (Japanese Patent Nos. 2572554 and 2659136) and the like.

The surface of the liposome may be modified with a polyhydric alcohol ester nonionic surfactant, an anionic surfactant, a cationic surfactant, an ampholytic surfactant, polysaccharides or derivatives thereof, polyoxyethylene derivatives and the like. Such a surface-modified liposome is included in the fine particle of the present invention [D. D. Lasic and F. Martin, *Stealth Liposomes*, U.S.A., CRC Press Inc, p. 93-102 (1995)].

The average particle diameter of the liposome is preferably 30 to 3,000 nm, more preferably 50 to 500 nm, and most preferably 60 to 200 nm. The method for controlling the average particle diameter of the liposome includes, for example, a method mechanically grounding large multilayer liposomes (MLV) by an extrusion method or by using a Manton Gaulin, a microfluidizer or the like. [R. H. Muller, S. Benita, and B. Bohm, *Emulsion and Nanosuspensions for the Formulation of Poorly Soluble Drugs*, Germany, Scientific Publishers Stuttgart, p. 267-294 (1998)] and the like.

In order to increase the retention in blood of the fine particle, generally, Compound (I) or a salt thereof is preferably contained in the fine particle at an amount of about 0.01 to 50 mol %, more preferably 0.1 to 20 mol %.

Furthermore, the above-described fine particle may be modified with a substance including a protein such as an antibody, saccharides, glycolipid, amino acid, nucleic acid, various low molecular weight compounds, a polymer and the like. Also, these substances may be incorporated into the above-described fine particle. The fine particles obtained by these metthods are included in the fine particle of the present invention. Additionally, the lipid membrane surface of the above-described fine particle may be modified with an antibody, a protein, a peptide, fatty acid or the like for application in targeting [D. D. Lasic and F. Martin, *Stealth Liposomes*, U.S.A., CRC Press Inc, p. 93-102 (1995)], and these lipid membrane surface-modified ones are also included in the fine particle of the present invention.

The fine particle of the present invention can hold or encapsulate, for example, a drug or the like, and can be used as a medicament for stabilizing the drug in the living body component such as blood component (e.g., blood, alimentary canal, etc.) reducing adverse sides, increasing accumulation of the drug in a target organ such as a tumor, or improving absorption of the drug in oral or transmucosal administration.

When the fine particle of the present invention is used as a medicament, for example, the drug held or encapsulated is not particularly limited, and examples include an antitumor agents, a contrast medium, an antibiotic, an antifungal agent, a substance having pharmacological activity, a biogenic substance and the like.

The antitumor agent includes, for example, actinomycin D, mitomycin C, chromomycin, doxorubicin, epirubicin, vinorelbine, daunorubicin, aclarubicin, bleomycin, peplomycin, vincristine, vinblastine, vindesine, etoposide, methotrexate, 5-Fu, tegafur, cytarabine, enocitabine, ancitabine, taxol, taxotere, cisplatin, cytosine arabinoside, irinotecan, camptothecin, derivatives thereof and the like.

The contrast medium includes, for example, iohexal, iodixanol, indocyanine green, sodium iothalamate and the like.

The antibiotic includes, for example, minocycline, tetracycline, piperacillin sodium, sultamicillin tosylate, amoxicillin, ampicillin, bacampicillin, aspoxicillin, cefdinir, flomoxef sodium, cefotiam, cefcapene pivoxil, cefaclor, cefditoren pivosil, cefazolin sodium, cefazoran, clarithromycin, clindamycin, erythromycin, levofloxacin, tosufloxacin tosylate, ofloxacin, ciprofloxacin, arbekacin, isepamicin, dibekacin, amikacin, gentamicin, vancomycin, phosphomycin, derivatives thereof and the like.

The antifungal agents include, for example, fluconazole, itraconazole, terbinafine, amphotericin B, miconazole, derivatives thereof and the like.

The substance having pharmacological activity includes, for example, a hormone, an enzyme, a protein, a peptide, an amino acid, a nucleic acid, a gene, antisense RNA, antisense DNA, siRNA (small interfering RNA), vitamins, saccharides, lipid, a synthetic medicament and the like.

The biogenic substance includes, for example, blood component and the like.

In the case of using the fine particle of the present invention as a medicament, the suspension of the fine particle prepared in the above method is directly used as an injection as it is, and the suspension can be used by processing it to the form of an oral agent, a nasal drop, an eye drop, a percutaneous agent, a suppository, an inhalant or the like. They can be produced by a usual method using a diluent, a vehicle, a disintegrating agent, a lubricant, a binder, a surfactant, water, a physiological saline solution, a vegetable oil-solubilizer, an isotonizing agent, a preservative, an antioxidant and the like which are pharmaceutically acceptable.

For example, the suspension of the fine particle may be converted to an oral agent such as a capsule, a tablet, or a granule agent by freeze-drying the suspension after adding a vehicle such as lactose or freeze-preserving it after adding a freeze preservative such as glycerin, followed by granulation, drying or the like together with an appropriate vehicle according to a usual method.

The effects of the present invention is described based on Test Examples, but the present invention is not limited thereto.

Test Example 1

Average Particle Diameter of Liposome:

The average particle diameters of the liposomes prepared in each of Examples 5 to 8 and Comparative Examples 1 to 3 were measured by an electrophoresis light scattering photometer (ELS) (A model ELS-800, manufactured by Otsuka Electronics).

The results are shown in Table 1. In the cases of 2 lots, the average particle diameters of the first lot and the second lot are shown in this order.

TABLE 1

|  | Average particle diameter (nm) |
|---|---|
| Example 5 (2 Lots) | 114, 125 |
| Example 6 | 123 |
| Example 7 | 115 |
| Example 8 | 116 |
| Comparative Example 1 (2 Lots) | 109, 127 |
| Comparative Example 2 (2 Lots) | 118, 125 |
| Comparative Example 3 | 109 |

As is shown in Table 1, the glycerol derivative-modified liposomes containing Compounds (2) or (4) prepared in Examples 5 to 8 have the average particle diameters of approximately 120 nm, which are suitable as the liposomes.

Test Example 2

Drug Encapsulation Rate:

Each of the liposome suspensions prepared in Examples 5 to 8 and Comparative Examples 1 to 3 (hereinafter referred to as the liposome suspensions A) was subjected to ultracentrifugation (1 hour, 110,000×g, 25° C.). Each liposome suspension A and supernatant obtained in the ultracentrifugation (hereinafter referred to as the supernatant A) were dissolved in a mixed solvent of 2-propanol and water (8/2 volume/volume). The absorbance at 497 nm of each solution was measured using a spectrophotometer (U-3210, manufactured by Hitachi) to determine the amount of doxorubicin in the liposome suspensions A and supernatants A. Also, a liposome suspension having the same phospholipid concentration as the liposome suspensions A and containing no doxorubicin (hereinafter referred to as the liposome suspension B) was prepared, the absorbance of phosphatidylcholine (PC) in the liposome was measured in the same manner as described above. The doxorubicin encapsulation ratio of the liposome in each liposome suspension A was calculated by the following equation.

$$\text{Encapsulation ratio}(\%) = \frac{(A - B) - C}{(A - B)} \times 100 \qquad (1)$$

A: Absorbance of liposome suspension A
B: Absorbance of liposome suspension B
C: Absorbance of supernatant A In Comparative Example 3, the liposome remained in the ultracentrifugation supernatant, so that the encapsulation rate was calculated by the following equation. The phospholipid concentration was measured by using Phospholipid C-Test Wako (Wako Pure Chemical Industries)

$$\text{Encapsulation ratio}(\%) = \frac{[(A - B) - C]/(D - E)}{(A - B)/D} \times 100 \qquad (2)$$

A: Absorbance of liposome suspension A
B: Absorbance of liposome suspension B
C: Absorbance of supernatant A
D: Phospholipid concentration of liposome suspension A
E: Phospholipid concentration of supernatant A The results are shown in Table 2. In the cases of 2 lots, the encapsulation rates of the first lot and the second lot are shown in this order.

TABLE 2

| | Encapsulation rate (%) |
|---|---|
| Example 5 (2 Lots) | 95, 91 |
| Example 6 | 79 |
| Example 7 | 96 |
| Example 8 | 89 |
| Comparative Example 1 (2 Lots) | 99, 98 |
| Comparative Example 2 (2 Lots) | 95, 89 |
| Comparative Example 3 | 56 |

As shown in Table 2, the PEG-modified liposome prepared in Comparative Example 3 was poor in the doxorubicin encapsulation rate, and thus it is clear that the increased PEG-DSPE content results in remarkable reduction of the liposome stability to cause leakage of the doxorubicin. On the other hand, the glycerol derivative-modified liposomes prepared in Examples 5 to 8 were excellent in the doxorubicin encapsulation rate, and thus it is clear that these liposomes are excellent in stability. Thus, the liposome containing the compound of the present invention has an excellent stability, not depending on the content of Compound (1).

Test Example 3

Each of the liposome suspensions (the administration drug liquids) prepared in Examples 7 and 8 and Comparative Examples 1 to 3 was administered to Crj:CD (SD) IGS rats (weight: 200 to 300 g, 3 rats per group, in the case of 2 lots, the suspension was administered to 2 rats in the first lot and to 1 rat in the second lot) under diethyl ether inhalation anesthesia from the left tail vein (dose: doxorubicin 0.35 mg/kg). The blood of each rat was collected from the right tail vein with time by a capillary treated with heparin, and was centrifuged (5 minutes, 8,000×g, 4° C.) to give a blood plasma, and the content of the doxorubicin in the blood plasma was determined by the following method.

The resulting blood plasma was diluted 10-fold with a 0.075 mol/L hydrogen chrolide solution of a 2-propanol/water (9/1) mixed solvent, followed by stirring. The resulting diluted liquid was cooled with ice and centrifuged (10 minutes, 12,000×g, 4° C.), and the fluorescence intensities of the resulting supernatant were measured at an excitation wavelength of 500 nm and at a fluorescence wavelength of 550 nm by a spectrophotofluorometer. Also, in the same manner as the determination of the doxorubicin in the blood plasma, a blood plasma collected from a rat with no administration of liposome suspensions was diluted 200-fold and the fluorescence intensity was measured. Separately, a standard doxorubicin solution was prepared, and the fluorescence intensity thereof was measured to give a calibration curve. The doxorubicin contents of each blood plasma and each administration liquid were obtained based on the calibration curve, and the rate (%) of the doxorubicin remaining in the blood plasma to the total of the administered doxorubicin was obtained based on 7.8 mL of the blood plasma amount of 250 g weight rat [*Pharmaceutical Res.*, 10 1093-1095 (1993)]. Also, using a blood plasma doxorubicin content (%)-time curve, an area $AUC_{0-24hr}$ under the curve in 0 to 24 hours was obtained by a trapezoidal method. The $AUC_{0-24hr}$ value was 1 in the case of administering the unmodified liposome of Comparative Example 1, and the $AUC_{0-24hr}$ values of the other modified liposomes were measured. The results are shown in Table 3.

TABLE 3

| | $AUC_{0-24hr}$/unmodified liposome $AUC_{0-24hr}$ |
|---|---|
| Example 7 | 28.9 |
| Example 8 | 37.4 |
| Comparative Example 1 (unmodified liposome) | 1.0 |
| Comparative Example 2 | 24.8 |
| Comparative Example 3 | 21.3 |

As is shown in Table 3, the doxorubicin $AUC_{0-24hr}$ values obtained in the cases of administering the glycerol derivative-modified liposomes of Examples 7 and 8 was remarkably higher than that in the case of administering the unmodified liposome of Comparative Example 1. Also, the doxorubicin $AUC_{0-24hr}$ values obtained in the cases of administering the glycerol derivative-modified liposomes of Examples 7 and 8 was higher than that in the cases of administering the PEG-modified liposomes of Comparative Examples 2 and 3. Based on these results, it is considered that the glycerol derivative-modified liposomes are more effective than the PEG-modified liposomes for maintaining high doxorubicin contents in the blood plasmas. Thus, it is expected that a higher drug efficacy can be obtained by using the liposome containing the compound of the present invention as a drug carrier without increasing the amount of a drug administered. For example, in the case of using the liposome containing the compound of the present invention as a drug carrier for an antitumor agent, the amount of the drug to reach the tumor is increased to thereby achieve an effective medical treatment, reduction of adverse side reactions, and the like.

In comparison of the $AUC_{0-24hr}$ values of the PEG-modified liposomes with different PEG-DSPE contents prepared in Comparative Examples 2 and 3, the doxorubicin $AUC_{0-24hr}$ values were hardly changed by changing the PEG-DSPE contents. On the other hand, in comparison of the $AUC_{0-24hr}$ values of the glycerol derivative-modified liposomes containing Compound (4) in a different content prepared in Examples 7 and 8, the doxorubicin $AUC_{0-24hr}$ values were increased by changing the glycerol derivative contents of Compound (4). Thus, it is considered that, unlike the PEG-modified liposomes, the glycerol derivative-modified liposomes can have further improved drug carrier functions of retention in blood plasma, and the like.

The present invention is described based on Examples and Reference Examples, but the present invention is not limited thereto.

Example 1

Preparation of Compound (2):

The reaction scheme is shown below. In the reaction scheme, Bn represents benzyl; NHS represents N-hydroxysuccinimide; and DSPE represents distearoylphosphatidylethanolamine.

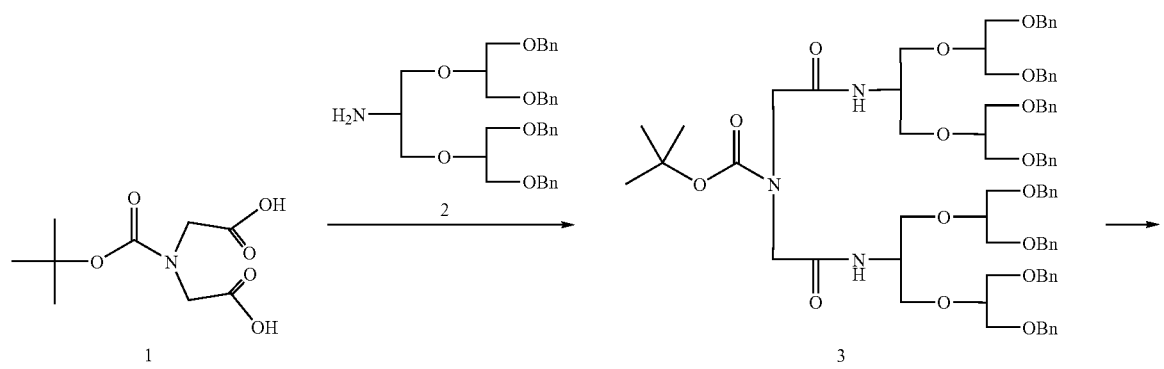
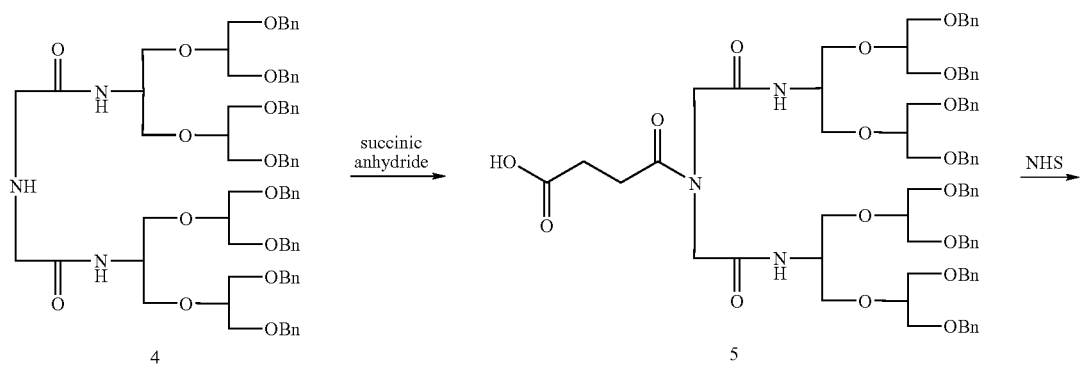
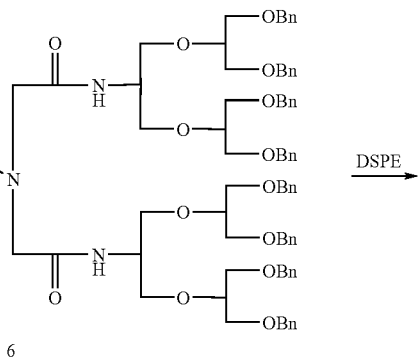
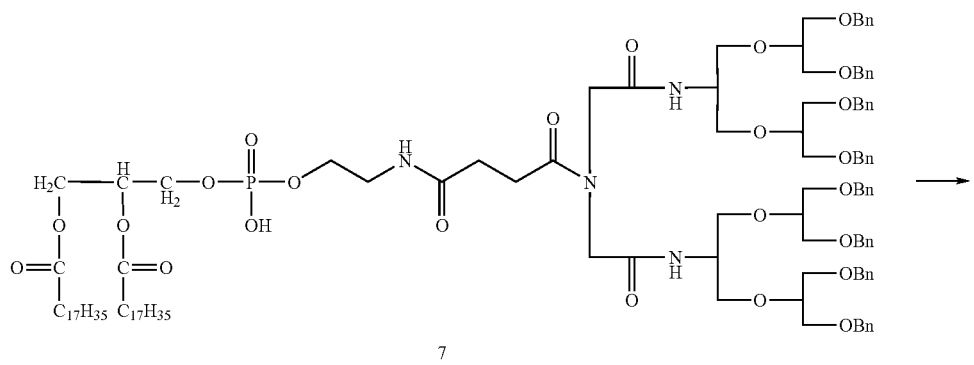

-continued

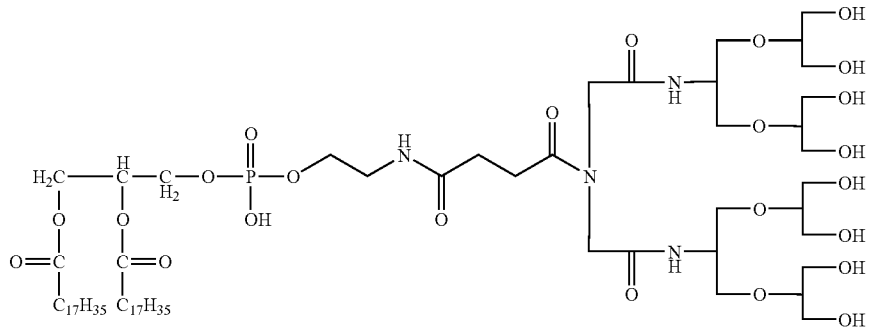

8

Compound 2 [2-amino-1,3-bis(1,3-di-O-benzyl-2-glyceroxy)propane] was prepared according to the method of Nemotor et al. [*J. Med. Chem.,* 38, 1673 (1995)]. Diisopropylethylamine (10.5 mL, 60.0 mmol), a DMF solution (20 mL) of Compound 2 (19.8 g, 33.0 mmol) and benzotriazol-1-yloxytris(pylidino)phosphonium hexafluorophosphine (PyBOP; 15.6 g, 30.0 mmol) were added to a dimethylformamide (DMF) solution (50 mL) of Compound 1 (3.5 g, 15.0 mmol) in this order at room temperature, followed by stirring at the same temperature for 15 hours. The reaction solution was poured into 5% aqueous potassium hydrogensulfate solution, followed by extraction with ethyl acetate. The organic layer was washed with a saturated aqueous sodium hydrogencarbonate solution and a saturated aqueous sodium chloride solution in this order, dried over and then filtered. The solvent was evaporated under reduced pressure, and the residue was purified by silica gel column chromatography (hexane:ethyl acetate=3:2) to give Compound 3 (18.7 g, yield 89%) as pale yellow oil.

$^1$H-NMR (CDCl$_3$, 300 MHz) δ (ppm): 1.36 (9H, s), 3.40-3.81 (32H, m), 4.16 (2H, m), 4.48 (16H, s), 7.19-7.31 (40H, m).

Trifluoroacetic acid (5 mL) was poured into a dichloromethane solution (45 mL) of Compound 3 (2.0 g, 1.43 mmol) at room temperature, followed by stirring at the same temperature for 20 hours. A saturated aqueous sodium hydrogencarbonate solution was added to the reaction solution, followed by extraction with dichloromethane. The organic layer was dried over anhydrous magnesium sulfate and filtered, and then the solvent was evaporated under reduced pressure to give Compound 4 (1.19 g, yield 64%) as pale yellow oil.

$^1$H-NMR (CDCl$_3$, 300 MHz) δ (ppm): 1.75 (1H, s), 2.87 (4H, s), 3.47-3.81 (28H, m), 4.16 (2H, m), 4.48 (16H, s), 7.00 (2H, d), 7.19-7.31 (40H, m).

Succinic anhydride (232 mg, 2.31 mmol) was gradually added to a pyridine solution (2.0 mL) of Compound 4 (1.5 g, 1.16 mmol) at room temperature, followed by stirring at 100° C. for 1.5 hours. The reaction solution was cooled to room temperature, and 2 mol/L hydrochloric acid was added thereto, followed by extraction with dichloromethane. The organic layer was washed with a saturated aqueous sodium chloride solution, dried over anhydrous magnesium sulfate and then filtered. The solvent was evaporated under reduced pressure, and the residue was purified by silica gel column chromatography (hexane:ethyl acetate=1:3) to give Compound 5 (1.62 g, yield 100%) as pale yellow oil.

$^1$H-NMR (CDCl$_3$, 300 MHz) δ (ppm): 2.39 (2H, m), 2.56 (2H, m), 3.45-3.76 (32H, m), 4.09-4.21 (2H, m), 4.46 (16H, s), 6.87 (1H, d), 7.19-7.31 (40H, m), 8.02 (1H, d).

N-hydroxysuccinimide (NHS; 495 mg, 4.30 mmol), 1-ethyl-3-(3-dimethylaminopropyl)carbodiimide hydrochloride (EDC; 886 mg, 4.30 mmol) and triethylamine (0.24 mL, 1.72 mmol) were added to a tetrahydrofuran solution (45 mL) of Compound 5 (3.0 g, 2.15 mmol) in this order at room temperature, followed by refluxing for 2 hours. Then, 5% aqueous potassium hydrogensulfate solution was added thereto, followed by extraction with dichloromethane. The organic layer was washed with a saturated aqueous sodium hydrogencarbonate solution and a saturated aqueous sodium chloride solution in this order, dried over anhydrous magnesium sulfate and then filtered. The solvent was evaporated under reduced pressure, and the residue was purified by silica gel column chromatography (hexane:ethyl acetate=1:10) to give Compound 6 (2.35 g, yield 79%) as pale yellow oil.

$^1$H-NMR (CDCl$_3$, 300 MHz) δ (ppm): 2.49 (2H, t), 2.67 (4H, s), 2.78 (2H, t), 3.40-3.78 (32H,m), 4.11-4.22 (2H, m), 4.48 (16H, d), 6.96 (1H, d), 7.19-7.31 (40H, m), 8.37 (1H, d).

Distearoylphosphatidylethanolamine (DSPE; 497 mg, 0.664 mmol) was dissolved in a mixed solvent of dichloromethan (50 mL) and methanol (50 mL) and a chlorofolm solution (50 mL) of Compuond 6 (993 mg, 0.665 mmol) was added thereto. To the reaction mixture, dichloromethane (50 mL) containing TEA (184 µl) was added, followed by stirring under shading and argon atmosphere at room temperature for 18 hours. The solvent was evaporated under reduced pressure and the residue was purified by silica gel column chromatography (methanol:chroroform=0:100, 1:50, 1:40, 1:30, 1:20, 1:10, 1:7.5 or 1:5 was applied in this order) to give Compound 7 (1.032 g, 0.4857 mmol. yield 73.1%).

$^1$H-NMR (CDCl$_3$, 300 MHz) δ (ppm): 0.85-0.90 (6H, t), 1.00-1.35 (64H, m), 2.20-2.24 (2H, t), 2.45-2.52 (2H, m), 3.30-3.92 (32H, m), 4.11-4.22 (2H, m), 4.44 (16H, d), 7.19-7.31 (40H, m).

Pd(OH)$_2$/C (Pd content: 20% by weight, 516 mg) was added to a methanol solution (50 mL) of Compound 7 (1.032 g, 0.4857 mmol) under hydrogen atmosphere at room temperature, followed by stirring at the same temperature for 6 hours. The reaction solution was filtered through a filter, and then the solvent was evaporated under reduced pressure to give Compound 8 (603 mg, yield 88.3%).

$^1$H-NMR (CDCl$_3$, 300 MHz) δ (ppm): 0.84-0.88 (6H, t), 1.10-1.40 (64H, m), 2.26-2.33 (2H, m), 2.55-2.63 (2H, m), 3.30-3.95 (32H, m), 4.14-4.23 (2H, m). FAB-MS: m/z 1404.8 ([M-H]$^-$, FAB$^-$)

Example 2

Preparation of Compound (4):

The reaction scheme is shown below. In the reaction scheme, Bn represents benzyl; NHS represents N-hydroxysuccinimide; and DSPE represents distearoylphosphatidylethanolamine.

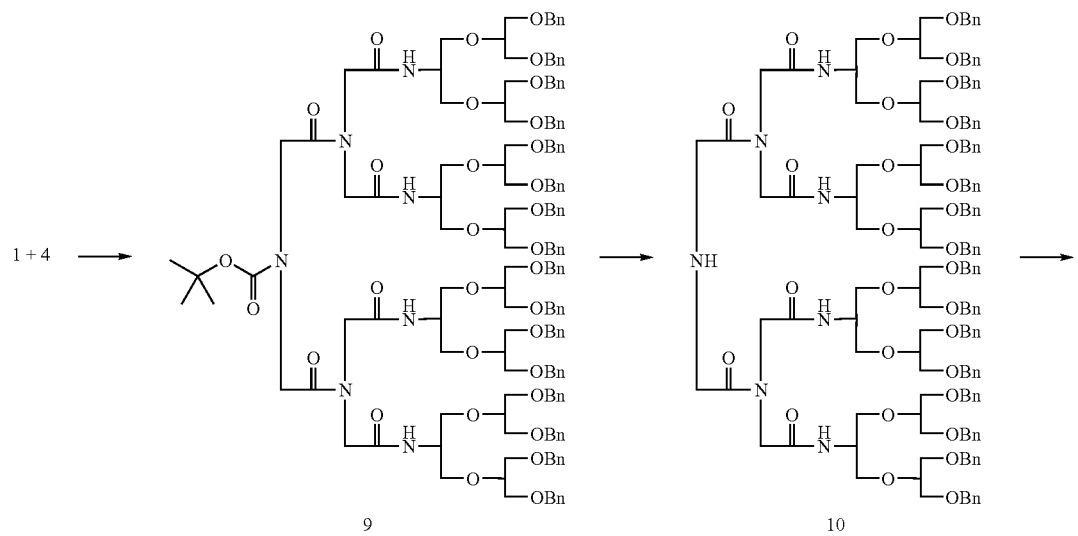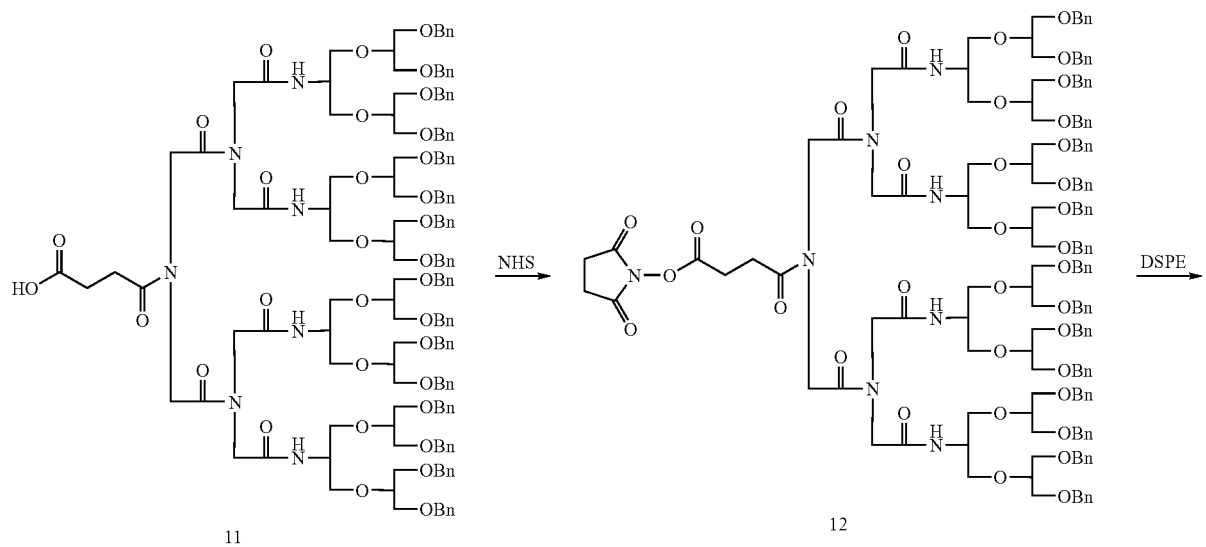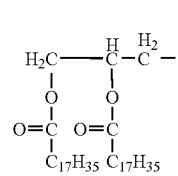

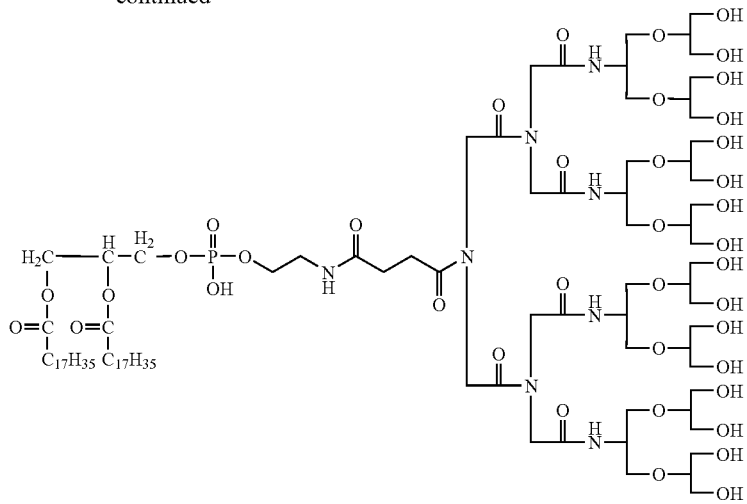

14

Compound 1 (51 mg, 0.219 mmol), diisopropylethylamine (0.15 mL, 0.876 mmol) and PyBOP (228 mg, 0.428 mmol) were added to a DMF solution (13 mL) of Compound 4 (624 mg, 0.48 mmol) at room temperature, followed by stirring at the same temperature for 48 hours. The reaction mixture was poured into 5% aqueous potassium hydrogensulfate solution, followed by extraction with ethyl acetate, and the organic layer was washed with a saturated aqueous sodium hydrogencarbonate solution and a saturated aqueous sodium chloride solution in this order. Thereafter, the organic layer was dried over anhydrous magnesium sulfate and filtered, and then the solvent was evaporated under reduced pressure. The residue was purified by using silica gel column chromatography (ethyl acetate:acetic acid=100:0.7) to give Compound 9 (322 mg, 0.115 mmol, yield 53%) as yellow oil.

$^1$H-NMR (CDCl$_3$, 400 MHz) δ (ppm): 7.32-7.17 (80H, m), 4.49-4.38 (32H, m), 4.15-4.06 (4H, m), 3.77-3.27 (68H, m), 1.32 (9H, s), (CONH was not clearly identified). $^{13}$C-NMR (CDCl$_3$, 75 MHz) δ (ppm): 170.2 (C×4, CONH), 167.7 (C×2, CON), 155.4 (C, O$_2$CN), 138.2 (CH×16), 128.3 (CH×16), 128.3 (CH×16), 127.7 (CH×16), 127.6 (CH×16), 127.6 (CH×16), 80.5 (C), 78.7 (CH×8), 73.2 (CH$_2$×16), 70.2 (CH$_2$×16), 68.9 (CH$_2$×8), 52.1 (CH$_2$×2), 51.9 (CH$_2$×4), 49.6 (CH×4), 28.2 (CH$_3$3).

Trifluoroacetic acid (0.48 mL) was added dropwise to a dichloromethane solution (48.32 mL) of Compound 9 (322 mg, 0.115 mmol) at room temperature. After stirring at the same temperature for 24 hours, the reaction solution was poured into a saturated aqueous sodium hydrogencarbonate solution, followed by extraction with dichloromethane, the organic layer was dried over anhydrous magnesium sulfate and filtered, and then the solvent was evaporated under reduced pressure to give Compound 10 (310 mg, 0.115 mmol, yield 100%) as white oil. This product was subjected to subsequent reaction without purification.

$^1$H-NMR (CDCl$_3$, 400 MHz) δ (ppm): 7.33-7.18 (80H, m), 4.50-4.39 (32H, m), 4.20-4.02 (4H, m), 3.94-3.28 (68H, m), (NH was not clearly identified), (CONH was not clearly identified).

Succinic anhydride (28 mg, 0.28 mmol) and N,N-dimethylaminopyridine (4 mg, 0.036 mmol) were added to a pyridine solution (3 mL) of Compound 10 (190 mg, 0.071 mmol) at room temperature, followed by stirring at 50° C. for 5 hours. The reaction solution was added to 2 mol/L aqueous hydrochloric acid solution, followed by extraction with dichloromethane. The organic layer was washed with a saturated aqueous sodium chloride solution, dried over anhydrous magnesium sulfate and filtered, and then the solvent was evaporated under reduced pressure. The residue was purified by using silica gel column chromatography (ethyl acetate: acetic acid=100:0.7) to give Compound 11 (150 mg, 0.054 mmol, yield 76%) as white oil.

$^1$H-NMR (CDCl$_3$, 400 MHz) δ (ppm): 7.35-7.17 (80H, m), 4.50-4.39 (32H, m), 4.22-4.05 (4H, m), 4.02-3.27 (68H, m), 2.62-2.53 (4H, m), (neither OH nor CONH was clearly identified).

NHS (12 mg, 0.11 mmol) was added to a tetrahydrofuran solution (2 mL) of Compound 11 (150 mg, 0.054 mmol) at room temperature, followed by stirring at the same temperature for 15 minutes, and then EDC (21 mg, 0.11 mmol) and triethylamine (7 mL, 0.043 mmol) were added thereto at room temperature, followed by refluxing for 30 minutes. The reaction solution was added to 5% aqueous KHSO$_4$ solution, followed by extraction with dichloromethane, the organic layer was washed with a saturated aqueous sodium hydrogencarbonate solution and a saturated aqueous sodium chloride solution in this order, dried over anhydrous magnesium sulfate and filtered, and then the solvent was evaporated under reduced pressure. The residue was purified by using flash column chromatography (ethyl acetate:hexane=20:1) to give Compound 12 (62 mg, 0.21 mmol, yield 40%) as oil.

$^1$H-NMR (CDCl$_3$, 400 MHz) δ (ppm): 7.39-7.18 (80H, m), 4.54-4.38 (32H, m), 4.23-4.07 (4H, m), 4.89-3.33 (68H, m), 2.77-2.69 (4H, m), 2.57-2.49 (4H, m), (CONH was not clearly identified).

$^{13}$C-NMR (CDCl$_{13}$, 75 MHz) δ (ppm): 172.1 (C, CO$_2$—), 170.4 (C, CON), 169.5 (C×4, CONH), 168.7 (C×2, CON), 168.1 (C×2, CON), 138.8 (C×16), 129.0 (CH×16), 129.0 (CH×16), 128.2 (CH×16), 128.0 (CH×16), 127.6 (CH×16), 79.3 (CH×8), 73.8 (CH$_2$×16), 70.5 (CH$_2$×16), 68.9 (CH$_2$×8), 52.1 (CH$_2$×2), 51.9 (CH$_2$×4), 50.4 (CH×4), 30.3 (CH$_2$), 30.2 (CH$_2$), 25.9 (CH$_2$×2).

TOF-MS: precision mass spectrometry (M)=2886, measured value (M+1)=2887.44

DSPE (39 mg, 0.052 mmol) was added to a mixture solvent of dichloromethane (10 mL) and methanol (5 mL) and a chloroform solution (5 mL) of Compound 12 (150 mg, 0.052 mmol) and TEA (4 μL) were added thereto. The reaction mixture was stirred under shading and argon atmosphere at room temperature for 18 hours. To the reaction solution, DSPE (20 mg) was further added, followed by stirring at 33° C. for 23 hours. The solvent was evaporated under reduced pressure and the residue was purified by silica gel column chromatography (methanol:chloroform=0:100, 1:50, 1:40, 1:30, 1:20, 1:10, 1:7.5 or 1:5 was applied in this order) to give Compound 13 (42.4 mg, 0.0121 mmol, yield 23.3%).

$^1$H-NMR (CDCl$_3$, 300 MHz) δ (ppm): 0.82-0.93 (6H, t), 1.10-1.35 (64H, m), 2.10-2.25 (2H, m), 3.50-3.65 (68H, m), 4.08-4.23 (2H, m), 4.43 (32H, d), 7.23-7.25 (80H, m).

Pd(OH)$_2$/C (Pd content: 20% by weight, 22 mg) was added to a methanol solution (2.2 mL) of Compound 13 (42.4 mg, 0.0121 nmol) under hydrogen atmosphere at room temperature, followed by stirring at the same temperature for 7 hours and at 30° C. for 17 hours. To the reaction solution, THF (1 mL) was added, followed by stirring at 30° C. for 6 hours and at 40° C. for 21 hours, and then 20 mg of 10% Pd-carbon powder was added thereto, followed by stirring at 40° C. for 95.5 hours. The reaction solution was filtered through a filter, and then the solvent was evaporated under reduced pressure to give Compound 14 (17.2 mg, yield 68.7%).

$^1$H-NMR (CD$_3$OD, 300 MHz) δ (ppm): 0.75-0.85 (6H, t), 1.10-1.30 (64H, m), 3.20-3.52 (68H, m).

TOF-MS: m/z 2076.2 ([M-H]$^-$, ES$^-$)

Example 3

Preparation of Compound (5) (First Method)

The reaction scheme is shown below. In the reaction scheme, Ph represents a phenyl group; Ts represents a p-toluenesulfonyl group; NHS represents N-hydroxysuccinimide; and DSPE represents distearoylphosphatidylethanolamine.

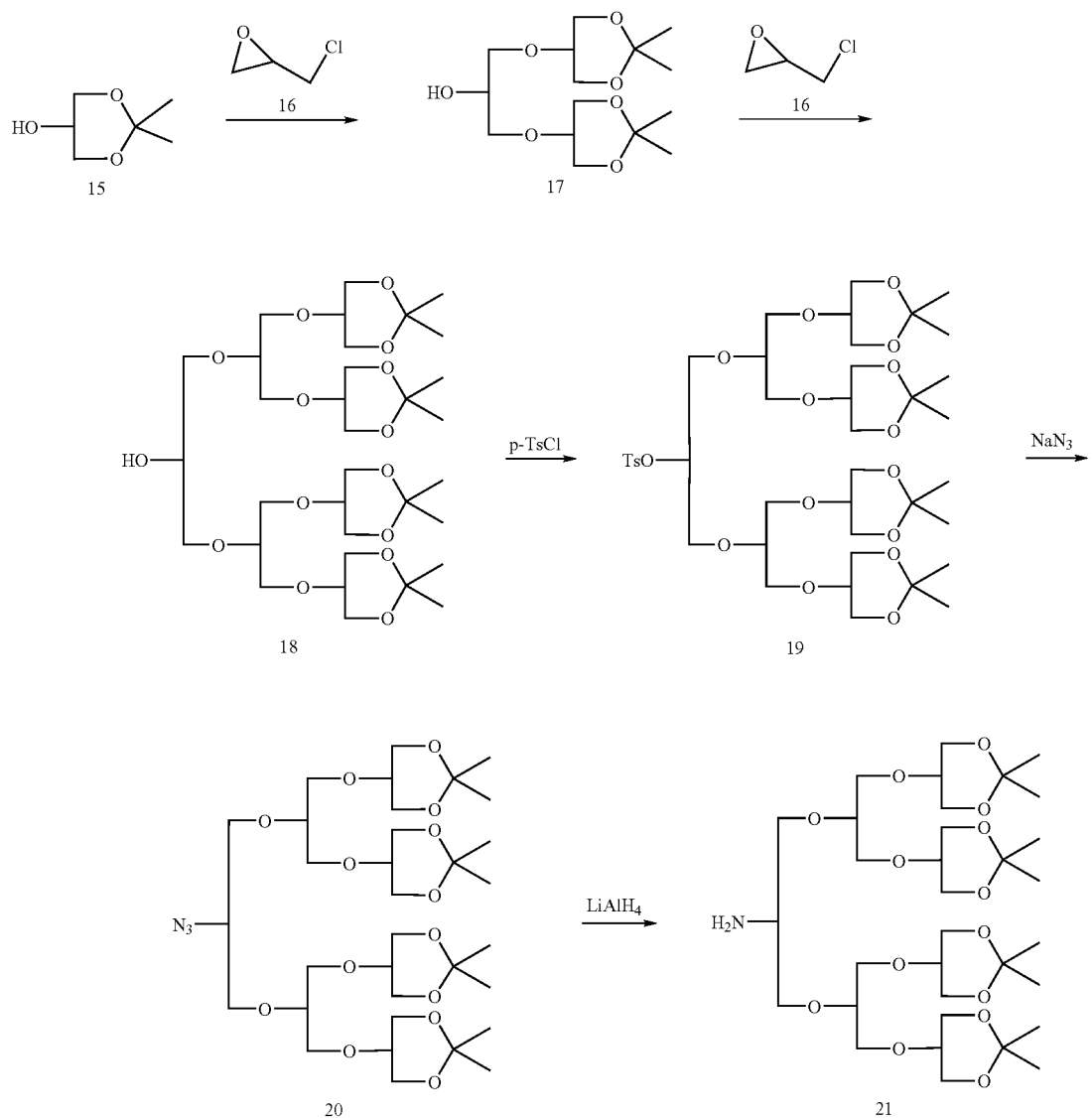

-continued
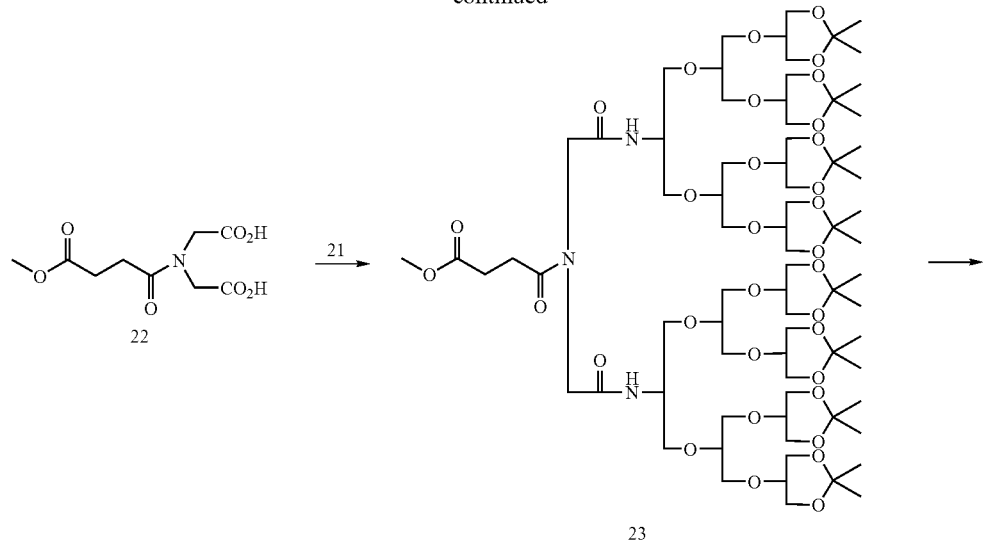
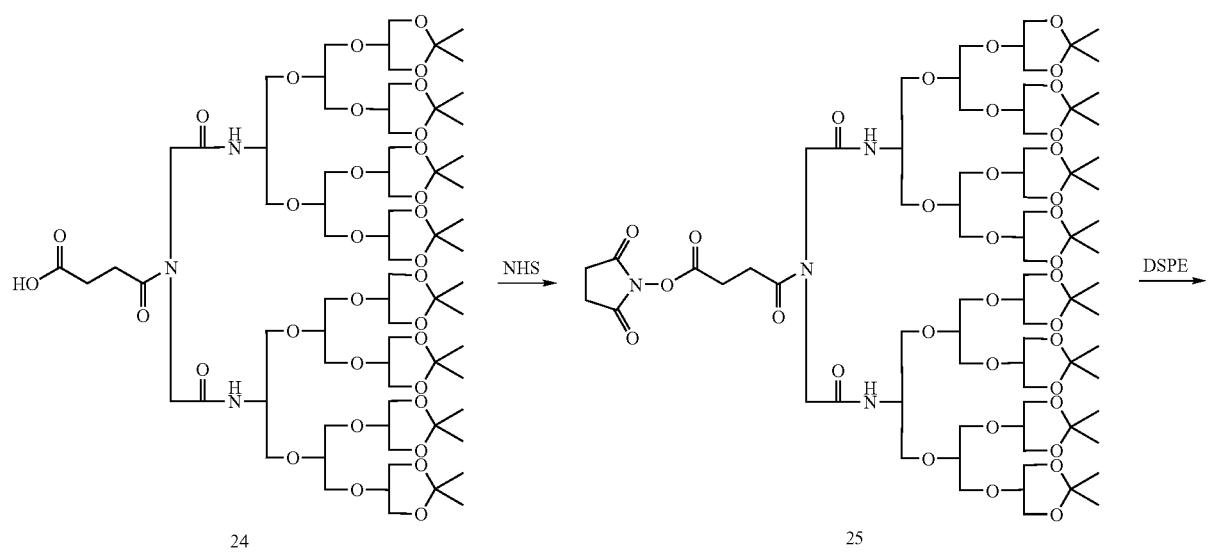
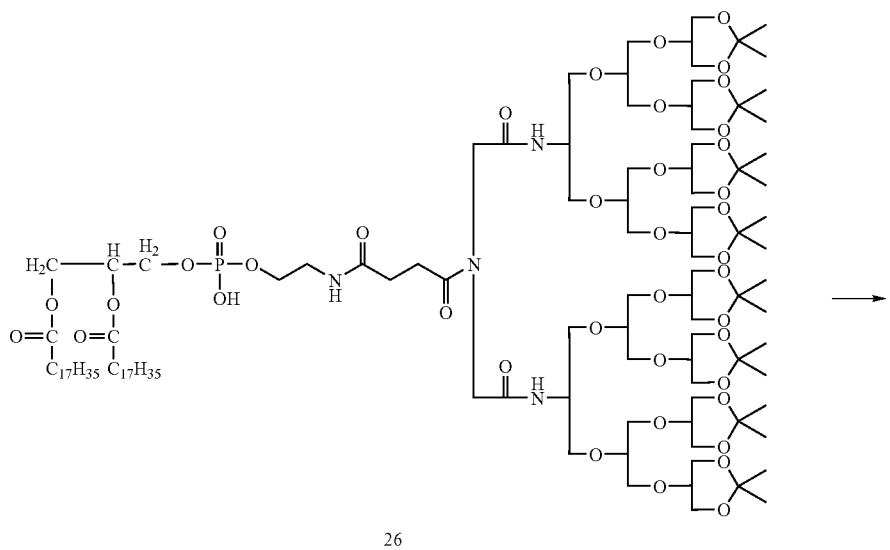

-continued

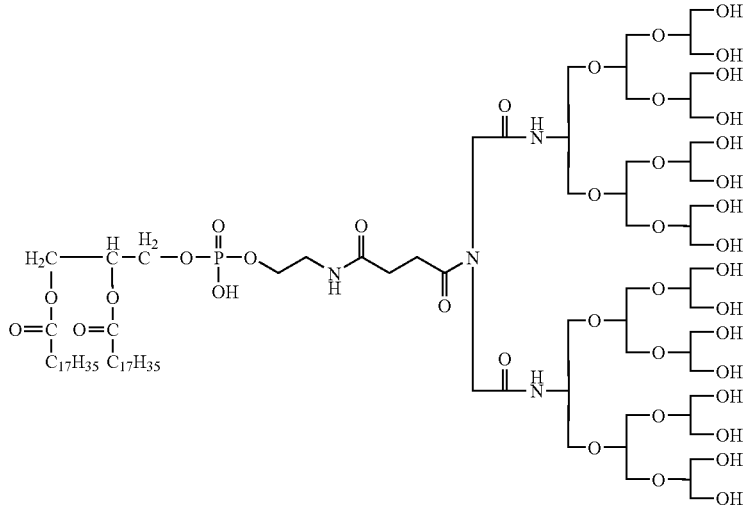

27

Compound 15 was prepared according to a known method [*Synthesis*, p. 879-882 (1998)]. Compound 16 (43.8 mg, 0.47 mmol) was slowly added dropwise to a suspension of Compound 15 (250.0 mg, 1.89 mmol), tetrabutylammonium bromide (30.5 mg, 0.09 mmol), potassium hydroxide (93.7 mg, 1.42 mmol) and water (0.04 mL) under vigorously stirring the suspension at room temperature. The reaction mixture was stirred at 60° C. for 40 hours, diluted with ethyl acetate (150 mL), and filtered. The filtrate was dried over anhydrous magnesium sulfate and then concentrated under reduced pressure. The residue was purified by silica gel column chromatography to give Compound 15 (130 mg, recovery 52%) and Compound 17 (64.8 mg, yield 43%).

$^1$H-NMR (400 MHz, CDCl$_3$): 4.05-3.70 (m, 9H), 3.65-3.45 (m, 4H), 3.45-3.41 (m, 2H), 2.63 (br, 1H), 1.43 (s, 6H), 1.41 (s, 6H)

$^{13}$C-NMR (100 MHz, CDCl$_3$): 98.1 (C×2), 70.8 (CH×2), 69.8 (CH$_2$×2), 69.4 (CH), 62.3 (CH$_2$×2), 62.2 (CH$_2$×2), 23.9 (CH$_3$×2), 22.9 (CH$_3$×2)

Compound 16 (72.2 mg, 0.78 mmol) was slowly added dropwise to a suspension of Compound 17 (1,000 mg, 3.12 mmol), tetrabutylammonium bromide (50.3 mg, 0.16 mmol), potassium hydroxide (154.5 mg, 2.34 mmol) and water (0.4 mL) under vigorously stirring at room temperature. The reaction mixture was stirred at 80° C. for 48 hours, water was added thereto, and the resulting suspension was extracted with methylene chrolide (80 mL, 5 times). The collected organic layer was dried over anhydrous potassium carbonate and then concentrated under reduced pressure. The residue was purified by silica gel column chromatography to give Compound 17 (273.2 mg, recovery 27%) and Compound 18 (414.6 mg, yield 76%).

$^1$H-NMR (CDCl$_3$, 400 MHz): 4.05-3.35 (m, 35H), 1.43 (s, 12H), 1.40 (s, 12H)

$^{13}$C-NMR (100 MHz, CDCl$_3$): 98.1 (C×4), 78.7 (CH×2), 71.9 (CH$_2$×2), 70.9 (CH×4), 69.6 (CH), 68.7 (CH$_2$×2), 68.6 (CH$_2$×2), 62.4 (CH$_2$×2), 62.4 (CH$_2$×2), 62.3 (CH$_2$×2), 62.3 (CH$_2$×2), 30.9 (CH$_3$), 29.6 (CH$_3$), 24.0 (CH$_3$×2), 24.0 (CH$_3$), 23.1 (CH$_3$×2), 23.0 (CH$_3$)

p-Toluenesulfonyl chrolide (1.01 g, 5.32 mmol) and 4-dimethylaminopyridine (65.0 mg, 0.53 mmol) were added to a pyridine solution (1 mL) of Compound 18 (1.85 g, 2.66 mmol) at room temperature, followed by stirring 16 hours. Ethyl acetate was added to the resulting reaction solution, and the mixture washed with a saturated aqueous copper sulfate solution, a saturated aqueous sodium hydrogen carbonate solution and a saturated aqueous sodium chloride solution, dried over sodium sulfate, and concentrated under reduced pressure to give Compound 19. The resulting Compound 19, sodium azide (1.04 g, 16.0 mmol) and tetrabutylammonium bromide (85.8 mg, 0.27 mmol) were dissolved in DMF (5 mL), and the resulting solution was stirred at 120° C. for 20 hours. A saturated aqueous sodium hydrogen carbonate solution was added to the resulting reaction solution, followed by extraction with ethyl acetate (3 times). The extract was washed with a saturated aqueous sodium chloride solution, dried over potassium carbonate and concentrated under reduced pressure. The resulting residue was purified by silica gel column chromatography to give Compound 20 (1.2048 g, yield 63%).

$^1$H-NMR (CDCl$_3$, 400 MHz): 4.01-3.51 (m, 31H), 3.48-3.40 (m, 4H), 1.43 (s, 12H), 1.41 (s, 12H)

Lithium aluminum hydride (2.2 mg, 0.057 mmol) was added to an anhydride THF solution (0.5 mL) of Compound 20 (20.5 mg, 0.028 mmol) at 0° C., and the resulting suspension was stirred at room temperature for 15 hours. Ethyl acetate was added dropwise to the resulting reaction solution at 0° C. When generation of hydrogen gas was completed, water (0.1 mL) was added thereto, followed by filtering. The filtrate was dried over potassium carbonate and concentrated under reduced pressure. The resulting residue was purified by column chromatography to give Compound 21 (7.8 mg, yield 40%).

$^1$H-NMR (CDCl$_3$, 400MHz): 4.02-3.50 (m, 31H), 1.42 (s, 12H), 1.40 (s, 12H)

Diisopropylethyl amine, a DMF solution of Compound 21 and PyBOP were added to a DMF solution of Compound 22 in this order, followed by stirring. The reaction liquid is poured into 5% aqueous potassium hydrogen sulfate solution and extracted with ethyl acetate. The resulting organic layer is washed with a saturated aqueous sodium hydrogen carbonate solution and then with a saturated aqueous sodium chloride solution, dried over anhydrous magnesium sulfate and filtered. The solvent is evaporated under reduced pressure, and the residue is purified by silica gel column chromatography to give Compound 23.

Lithium oxide is slowly added to an aqueous solution of Compound 23 at room temperature, followed by stirring. The reaction liquid is extracted with dichloromethane. The organic layer is washed with a saturated aqueous sodium chloride solution, dried over anhydrous magnesium sulfate and filtered. The solvent is evaporated under reduced pressure, and the residue is purified by silica gel column chromatography to give Compound 24.

NHS, EDC and triethylamine are added to a DMF solution of Compound 24 in this order, followed by refluxing. Then, 5% aqueous potassium hydrogen sulfate solution is added to the reaction solution, followed by extraction with dichloromethane. The organic layer is washed with a saturated aqueous sodium hydrogen carbonate solution and then with a saturated aqueous sodium chloride solution, dried over anhydrous magnesium sulfate and filtered. The solvent is evaporated under reduced pressure, and the residue is purified by silica gel column chromatography to give Compound 25.

Compound 26 can be obtained using the resulting Compound 25 and DSPE in the same manner as the reaction of Compound 6 and DSPE in Example 1.

Compound 27 can be obtained by treating Compound 26 under acidic conditions, preferably under weak acidic conditions.

Example 4

Preparation of Compound (5) (Second Method)

The reaction scheme is shown below. In the reaction scheme, Ph represents a phenyl group; Ts represents a p-toluenesulfonyl group; NHS represents N-hydroxysuccinimide; and DSPE represents distearoylphosphatidylethanolamine.

Compound 28 was prepared according to a known method [*J. Am. Chem. Soc,* 117, 8757-8768 (1995)]. Compound 16 (0.91mL, d=1.183 g/L, 11.6 mmol) was slowly added dropwise to a suspension of Compound 28 (8.739 g, 48.5 mmol), tetrabutylammonium bromide (0.773 g, 2.33 mmol), potassium hydroxide (2.304 g, 41.1 mmol) and water (10 mL) under vigorously stirring at room temperature, followed by stirring at 80° C. for 40 hours. Then, water (200 mL) was added thereto, and the resulting suspension was extracted with methylene chrolide (80 L, 5 times). The recovered organic layer was washed with an aqueous sodium chloride solution, dried over anhydrous potassium carbonate and concentrated under reduced pressure, and the residue was purified by silica gel column chromatography to give Compound 28 (4.803 g, recovery 55%) and Compound 29 (2.939 g, yield 61%).

$^1$H-NMR (CDCl$_3$, 400 MHz): δ 7.54-7.29 (m, 10H, aromatic ring), 5.54 (s, 2H, [—CH$_2$O]$_2$—CHPh), 4.40-3.96 (m, 9H, [CH$_2$]×4+HOCH—), 3.77-3.67 (m, 4H, [CH$_2$]×2), 3.39-337 (m, 2H, [CH$_2$—O—CH]×2), 2.88-2.80 (m, 1H, —OH)

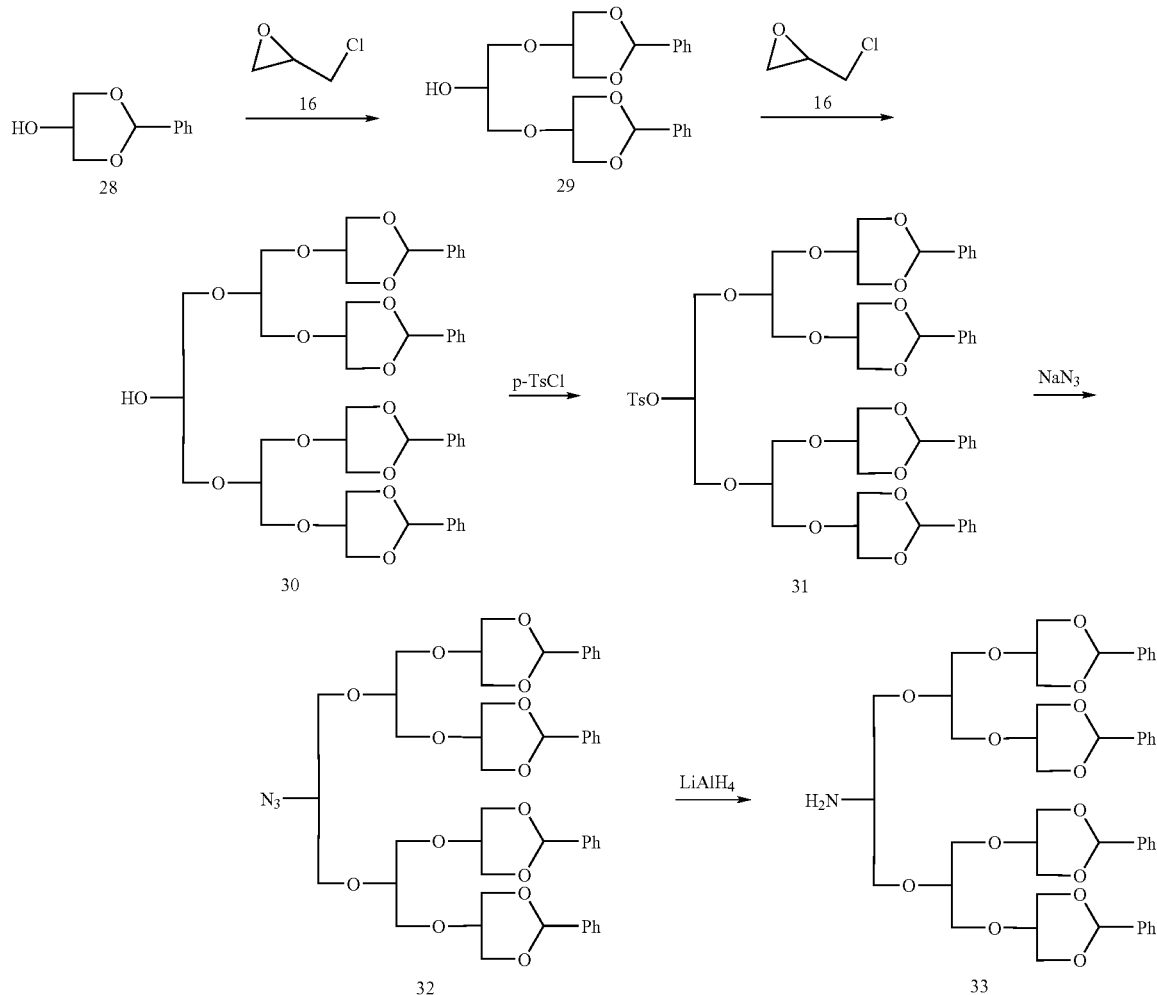

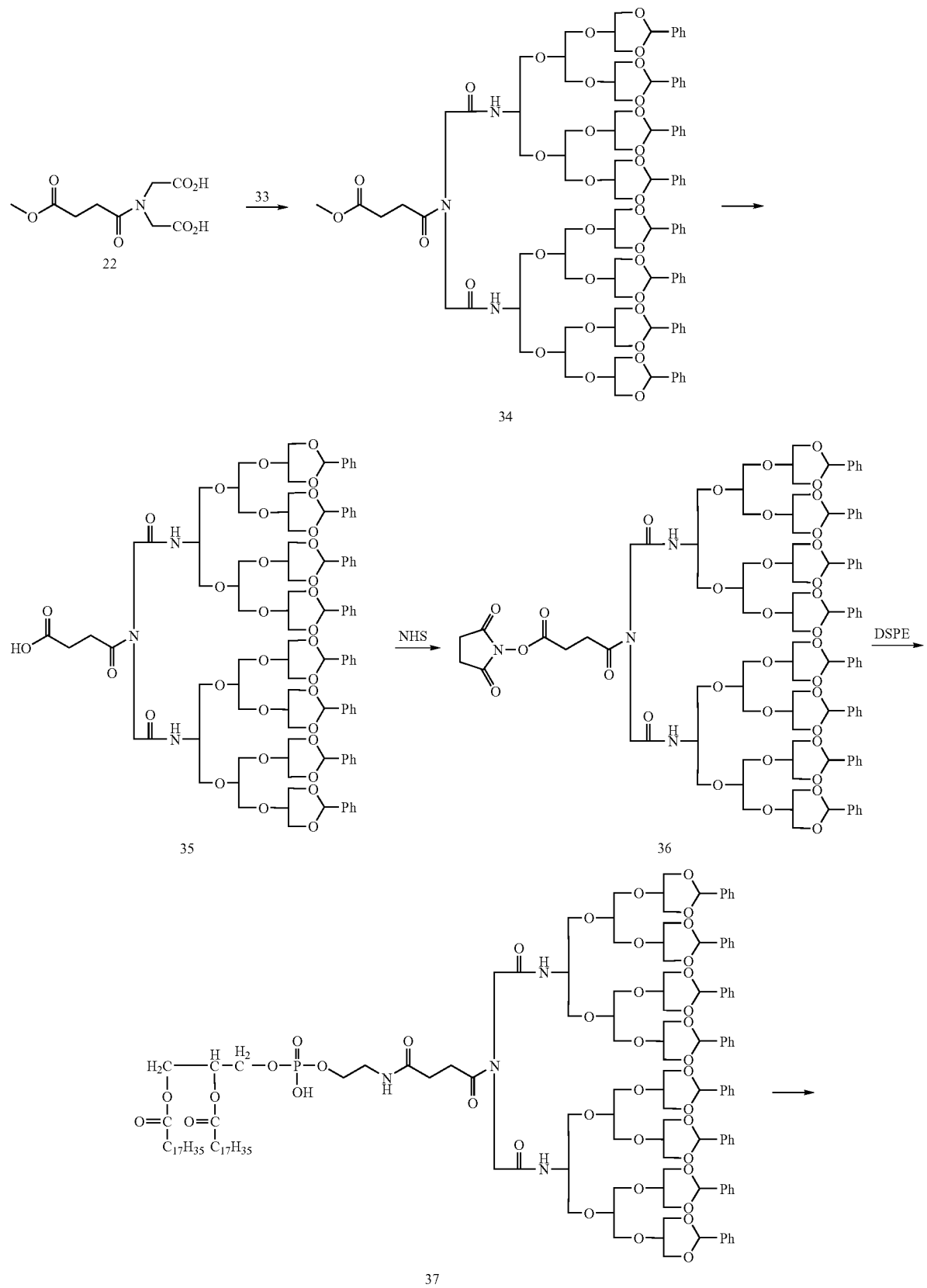

-continued

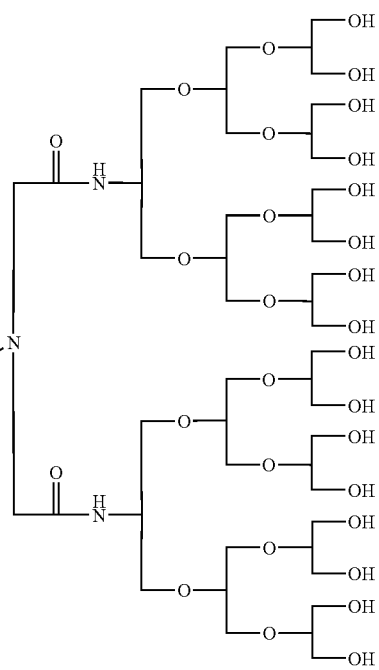

27

Compound 16

(0.087 mL, 1.11 mmol) was slowly added dropwise to a suspension of Compound 29 (1.844 g, 4.43 mmol), sodium hydride (55% in mineral oil dispersion, 0.145 g, 3.32 mmol) and dioxane (15 mL) under vigorously stirring at room temperature. The reaction mixture was stirred under refluxing for 43 hours, water (50 mL) was added thereto, and the resulting suspension was extracted with methylene chrolide (50 mL, 3 times). The recovered organic layer was washed with an aqueous sodium chloride solution, dried over anhydrous potassium carbonate and concentrated under reduced pressure. The residue was purified by silica gel column chromatography to give Compound 29 (1.106 g, recovery 60%) and Compound 30 (181 mg, yield 18%).

$^1$H-NMR (CDCl$_3$, 400 MHz): δ 6 7.70-7.28 (m, 20H, aromatic ring), 5.48 (s, 4H, [—CH$_2$O]$_2$—CHPh), 4.51-3.47 (m, 33H [CH$_2$]×14, [CH]×4, —OH), 3.32-3.30 (m, 3H, [CH]×3).

Compound 36 can be obtained using the resulting Compound 30 in the same manner as the reaction of Compound 18 and the reactions of Compounds 19 to 24 in Example 3.

Compound 37 can be obtained using Compound 36 and DSPE in the same manner as the reaction of Compound 6 and DSPE in Example 1.

Compound 27 can be obtained by treating Compound 38 in a methanol solution with Pd(OH)$_2$/C under hydrogen atmosphere at room temperature in the same manner as Compound 7 in Example 1.

Reference Example

Preparation of Compound 22

The reaction scheme is shown below. In the reaction scheme, Bn represents a benzyl group.

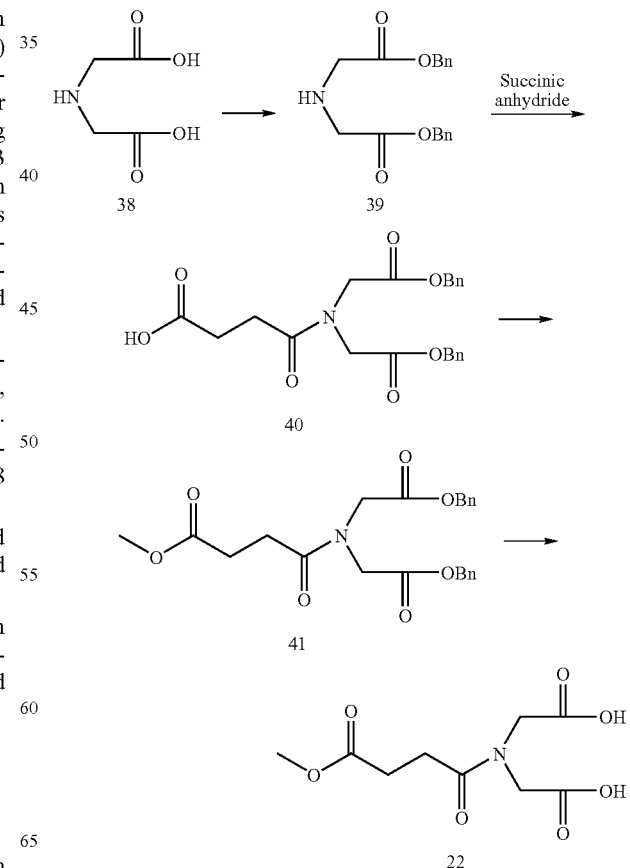

p-Toluenesulfonic acid monohydrate (1.80 g, 9.0 mmol) and benzylalcohol (31 mL, 301 mmol) were added to a toluene solution (20 mL) of Compound 38 (1.00 g, 7.5 mmol) in this order at a room temperature, followed by azeotropically dehydrating for 20 hours. Diethyl ether was added to the reaction solution, followed by cooling. The resulting precipitate was isolated by filtration and washed with diethyl ether. Methylene chrolide and a saturated aqueous sodium hydrogen carbonate solution were added thereto, followed by extraction with methylene chrolide. The organic layer was dried over anhydrous sodium sulfate and filtered, and the solvent was evaporated under reduced pressure to give Compound 39.

Succinic anhydride (1,125 mg, 11.25 mmol) was added to a pyridine solution (6 mL) of the resulting Compound 39 at room temperature, followed by stirring at the same temperature for 6 hours. To the reaction solution, 1 mol/L hydrochloric acid was added, and then the mixture was extracted with ethyl acetate. The organic layer was washed with a saturated aqueous sodium chloride solution, dried over anhydrous magnesium sulfate and filtered, and the solvent was evaporated under reduced pressure to give Compound 40.

Anhydrous potassium carbonate (2,073 mg, 15 mmol) and dimethyl sulfate (1,895 mg, 15 mmol) were added in this order to an acetone solution (50 mL) of the resulting compound 40 at room temperature, and the mixture was refluxed for 1 hour. Then, 5% aqueous potassium hydrogen sulfate solution was added to the reaction solution, followed by extraction with ethyl acetate. The organic layer was washed with a saturated aqueous sodium chloride solution, dried over anhydrous magnesium sulfate and filtered, the solvent was evaporated under reduced pressure, and the residue was purified by silica gel column chromatography (hexane:ethyl acetate=1:1) to give Compound 41 (545.0 mg, yield 17%).

$^1$H-NMR (400 MHz, CDCl$_3$): 7.44-7.29 (m, 10H), 5.22-5.12 (m, 4H), 4.27-4.20 (m, 4H), 3.68 (s, 3H), 2.70-2.60 (m, 4H)

Pd(OH)$_2$/C (Pd: 20 wt %, 25 mg) was added to a methanol solution (5 mL) of Compound 41 (535.8 mg, 1.25 mmol) under hydrogen stream at room temperature, followed by stirring for 2 hours at the same temperature. The reaction solution was filtered using celite 535, and the solvent was evaporated under reduced pressure to give Compound 22 (309.0 mg, yield 100%).

$^1$H-NMR (400 MHz, CD$_3$OD): 4.34-4.05 (m, 4H), 3.66 (s, 3H), 2.72-2.52 (m, 4H)

Example 5

Preparation of Glycerol Derivative-Modified Liposome Containing Compound (2) (Modification Rate 6.7 Mol %)

A 100 mmol/L citric acid buffer (pH 4.0) was added to a hydrogenated soy phosphatidylcholine (HSPC), followed by stirring under shaking with a Vortex mixer. The resulting suspension was filtered through a 0.4-μm polycarbonate membrane filter 4 times and filtered through a 0.1-μm polycarbonate membrane filter 10 times at 70° C. A 100 mmol/L citric acid buffer was added to the resulting solution, so that an unmodified liposome suspension was prepared to give the HSPC concentration of 62.5 mg/mL. The unmodified liposome suspension was added to doxorubicin to control the doxorubicin concentration at 1.25 mg/mL. The pH of the resulting suspension was adjusted to approximately 7.4 by using 1 mol/L aqueous sodium hydroxide solution, and distilled water was added to the suspension to give the doxorubicin concentration of 1 mg/mL. The resulting suspension was heated at 70° C. for 5 minutes to prepare a suspension of an unmodified liposome encapsulating doxorubicin. To the suspension of the unmodified liposome encapsulating the doxorubicin, an ethanol solution of Compound (2) prepared in Example 1 (ethanol content: 1 volume % of the suspension of the unmodified liposome encapsulating the doxorubicin) was added so that the mole rate of Compound (2) to the lipids in the desired glycerol derivative-modified liposome was 6.7 mol %. The resulting suspension was heated at 70° C. for 2 minutes to give a glycerol derivative-modified liposome containing Compound (2). Two lots of this liposome were prepared in this manner.

Example 6

Preparation of Glycerol Derivative-Modified Liposome Containing Compound (2) (Modification Rate 15 Mol %)

A 100 mmol/L citric acid buffer (pH 4.0) was added to HSPC, followed by stirring under shaking with a Vortex mixer. The resulting suspension was filtered through a 0.4-μm polycarbonate membrane filter 4 times and filtered through a 0.1-μm polycarbonate membrane filter 10 times at 70° C. A 100 mmol/L citric acid buffer was added to the resulting solution so that an unmodified liposome suspension was prepared to give the HSPC concentration of 62.5 mg/mL. The unmodified liposome suspension was added to doxorubicin to control the doxorubicin concentration at 1.25 mg/mL. The pH of the resulting suspension was adjusted to approximately 7.4 by using 1 mol/L aqueous sodium hydroxide solution, and distilled water was added to the suspension to give the doxorubicin concentration of 1 mg/mL. The resulting suspension was heated at 70° C. for 5 minutes to prepare a suspension of an unmodified liposome encapsulating doxorubicin. To the suspension of the unmodified liposome encapsulating the doxorubicin, an ethanol solution of Compound (2) prepared in Example 1 (ethanol content: 1 volume % of the suspension of the unmodified liposome encapsulating the doxorubicin) was added so that the mole rate of Compound (2) to the lipids in the desired glycerol derivative-modified liposome was 15 mol %. The resulting suspension was heated at 70° C. for 2 minutes to give a glycerol derivative-modified liposome containing Compound (2).

Example 7

Preparation of Glycerol Derivative Liposome Containing Compound (4) (Modification Rate 6.7 Mol %)

A 100 mmol/L citric acid buffer (pH 4.0) was added to HSPC, and the mixture was shaken and stirred by a Vortex mixer. The resulting suspension was filtered through a 0.4-μm polycarbonate membrane filter 4 times and filtered through a 0.1-μm polycarbonate membrane filter 10 times at 70° C. A 100 mmol/L citric acid buffer was added to the resulting solution, so that an unmodified liposome suspension was prepared such that the HSPC concentration was 62.5 mg/mL. The unmodified liposome suspension was added to doxorubicin to control the doxorubicin concentration at 1.25 mg/mL. The pH of the resulting suspension was adjusted to approximately 7.4 by using 1 mol/L sodium hydroxide aqueous solution, and distilled water was added to the suspension, so that the doxorubicin content was 1 mg/mL. The resulting suspension was heated at 70° C. for 5 minutes to prepare a suspension of an unmodified liposome encapsulating doxorubicin. To the suspension of the unmodified liposome encapsulating the doxorubicin was added the ethanol solution of Compound (4) prepared in Example 2 (ethanol content: 1 volume % of the suspension of the unmodified liposome encapsulating the doxorubicin) such that the mole rate of Compound (4) to the lipids in the desired glycerol derivative-modified liposome was 6.7 mol %. The resulting suspension was heated at 70° C. for 2 minutes to give a glycerol derivative-modified liposome containing Compound (4).

Example 8

Preparation of Glycerol Derivative-Modified Liposome Containing Compound (4) (Modification Rate 15 Mol %)

A 100 mmol/L citric acid buffer (pH 4.0) was added to HSPC, and the mixture was shaken and stirred by a Vortex mixer. The resulting suspension was filtered through a 0.4-μm polycarbonate membrane filter 4 times and filtered through a 0.1-μm polycarbonate membrane filter 10 times at 70° C. A 100 mmol/L citric acid buffer was added to the resulting solution, so that an unmodified liposome suspension was prepared to give the HSPC concentration of 62.5 mg/mL. The unmodified liposome suspension was added to doxorubicin to control the doxorubicin concentration at 1.25 mg/mL. The pH of the resulting suspension was adjusted to approximately 7.4 by using 1 mol/L sodium hydroxide aqueous solution, and distilled water was added to the suspension to give the doxorubicin concentration of 1 mg/mL. The resulting suspension was heated at 70° C. for 5 minutes to prepare a suspension of an unmodified liposome encapsulating doxorubicin. To the suspension of the unmodified liposome encapsulating the doxorubicin, an ethanol solution of Compound (4) prepared in Example 2 (ethanol content: 1 volume % of the suspension of the unmodified liposome encapsulating the doxorubicin) was added such that the mole rate of Compound (4) to the lipids in the desired glycerol derivative-modified liposome was 15 mol %. The resulting suspension was heated at 70° C. for 2 minutes to give a glycerol derivative-modified liposome containing Compound (4).

Comparative Example 1

Preparation of Unmodified Liposome

A 100 mmol/L citric acid buffer (pH 4.0) was added to HSPC, followed by shaking under stirring with a Vortex mixer. The resulting suspension was filtered through a 0.4-μem polycarbonate membrane filter 4 times and filtered through a 0.1-μm polycarbonate membrane filter 10 times at 70° C. A 100 mmol/L citric acid buffer was added to the resulting solution, so that an unmodified liposome suspension was prepared to give the HSPC concentration of 62.5 mg/mL. The unmodified liposome suspension was added to doxorubicin to control the doxorubicin concentration at 1.25 mg/mL. The pH of the resulting suspension was adjusted to approximately 7.4 by using 1 mol/L aqueous sodium hydroxide solution, and distilled water was added to the suspension to give the doxorubicin content of 1 mg/mL. The resulting suspension was heated at 70° C. for 5 minutes to prepare a suspension of an unmodified liposome encapsulating doxorubicin. Two lots of this liposome were prepared in this manner.

Comparative Example 2

Preparation of PEG-modified Liposome (Modification Rate 6.7 Mol %)

A 100 mmol/L citric acid buffer (pH 4.0) was added to HSPC, followed by stirring under shaking with a Vortex mixer. The resulting suspension was filtered through a 0.4-μm polycarbonate membrane filter 4 times and filtered through a 0.1-μm polycarbonate membrane filter 10 times at 70° C. A 100 mmol/L citric acid buffer was added to the resulting solution, so that an unmodified liposome suspension was prepared to give the HSPC concentration of 62.5 mg/mL. The unmodified liposome suspension was added to doxorubicin to control the doxorubicin concentration at 1.25 mg/mL. The pH of the resulting suspension was adjusted to approximately 7.4 by using 1 mol/L aqueous sodium hydroxide solution, and distilled water was added to the suspension to give the doxorubicin content of 1 mg/mL. The resulting suspension was heated at 70° C. for 5 minutes to prepare a suspension of an unmodified liposome encapsulating doxorubicin. To the suspension of the unmodified liposome encapsulating the doxorubicin, an ethanol solution of PEG-DSPE (1,2-distearoyl-sn-glycero-3-phosphoethanolamine-N-[poly(ethyleneglycol)-2000], available from Avanti) (ethanol content: 1 volume % of the suspension of the unmodified liposome encapsulating the doxorubicin) was added so that the mole rate of the PEG-DSPE to the lipids in the desired PEG-modified liposome was 6.7 mol %. The resulting suspension was heated at 70° C. for 2 minutes to give a PEG-modified liposome. Two lots of this liposome were prepared in this manner.

Comparative Example 3

Preparation of PEG-Modified Liposome (Modification Rate 15 Mol %)

A 100 mmol/L citric acid buffer (pH 4.0) was added to HSPC, followed by stirring under shaking with a Vortex mixer. The resulting suspension was filtered through a 0.4-μm polycarbonate membrane filter 4 times and filtered through a 0.1-μm polycarbonate membrane filter 10 times at 70° C. A 100 mmol/L citric acid buffer was added to the resulting solution, so that an unmodified liposome suspension was prepared to give the HSPC concentration of 62.5 mg/mL. The unmodified liposome suspension was added to doxorubicin to control the doxorubicin concentration at 1.25 mg/mL. The pH of the resulting suspension was adjusted to approximately 7.4 by using 1 mol/L sodium hydroxide aqueous solution, and distilled water was added to the suspension to give the doxorubicin concentration of 1 mg/mL. The resulting suspension was heated at 70° C. for 5 minutes to prepare a suspension of an unmodified liposome encapsulating doxorubicin. To the suspension of the unmodified liposome encapsulating the doxorubicin, an ethanol solution of PEG-DSPE available from Avanti (ethanol content: 1 volume % of the suspension of the unmodified liposome encapsulating the doxorubicin) was added so that the mole rate of the PEG-DSPE to the lipids in the desired PEG-modified liposome was 15 mol %. The resulting suspension was heated at 70° C. for 2 minutes to give a PEG-modified liposome.

INDUSTRIAL APPLICABILITY

The present invention provides a compound in which an amphiphilic or hydrophobic substance is modified with a glycerol derivative, which is useful as a surface modifier for producing a drug carrier or the like, or a salt thereof; a fine particle comprising the same; and the like.

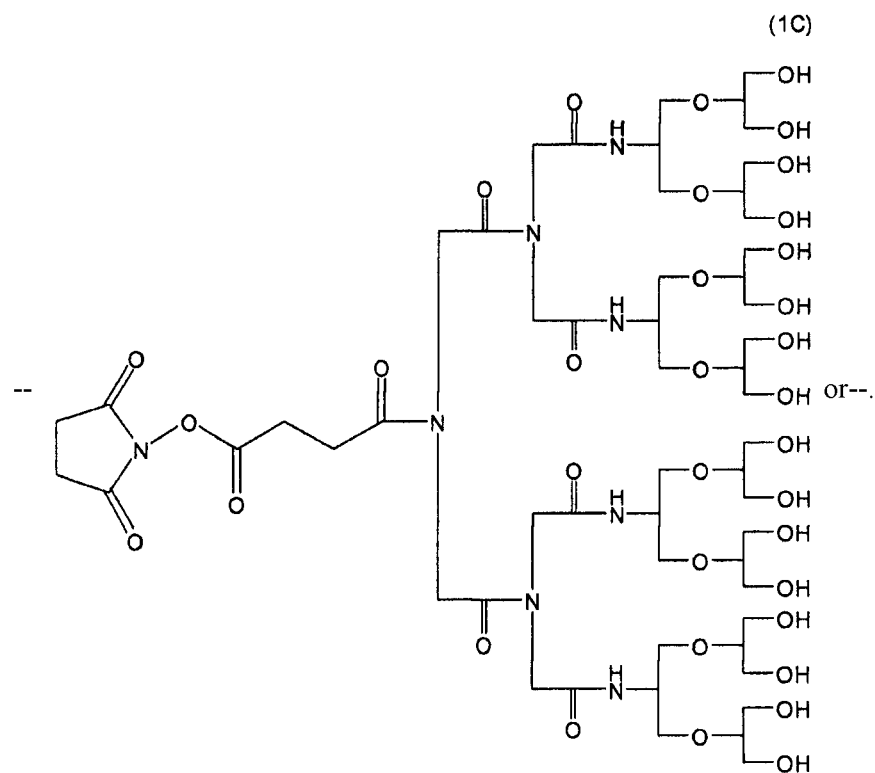

The invention claimed is:
1. A compound represented by formula (5):

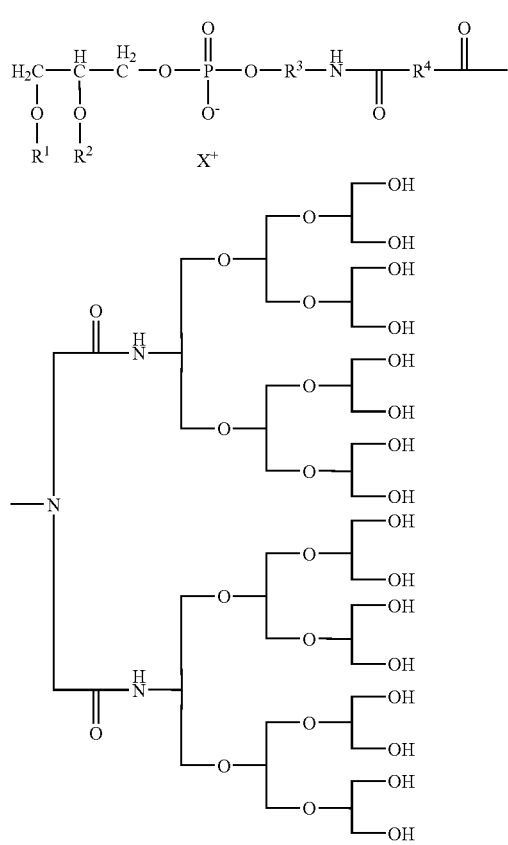

wherein X represents a hydrogen atom or an alkaline metal atom;

$R^1$ and $R^2$ independently represent a hydrogen atom, a straight chain or branched chain saturated fatty acid residue having an acyl moiety of 12 to 30 carbon atoms or a straight chain or branched chain unsaturated fatty acid residue having an acyl moiety of 12 to 30 carbon atoms, wherein at least one of $R^1$ and $R^2$ is the saturated fatty acid residue or the unsaturated fatty acid residue; and $R^3$ and $R^4$ independently represent alkylene having 1 to 10 carbon atoms, or a salt thereof.

2. The compound according to claim 1, wherein $R^3$ and $R^4$ are ethylene.

3. A fine particle comprising the compound according to claim 1 or a salt thereof.

4. The fine particle according to claim 3, wherein the fine particle is selected from the group consisting of a liposome, a fat emulsion, an emulsion, a micell and a fine particle crystal.

5. A fine particle comprising the compound of claim 2 or a salt thereof.

6. The fine particle according to claim 5, wherein the fine particle is selected from the group consisting of a liposome, a fat emulsion, an emulsion, a micell and a fine particle crystal.

7. A compound obtainable by linking, directly or via a spacer, (i) a substance selected from the group consisting of phospholipid, glyceroglycolipid, sphingoglycolipid, sphingoids, sterols, cationic lipid, anionic lipid, polyhydric alcohol ester nonionic surfactant, anionic surfactant, cationic surfactant, ampholytic surfactant, liquid paraffin, vegetable oil, ester of fatty acid having 12 to 30 carbon atoms, castor oil, polyoxyethylene castor oil, lanolin, polyaspartic acids, poly(β-benzyl aspartate), poly(γ-benzyl glutamate), poly(β-alkyl aspartate), polylactide, poly(ε-caprolactone), poly(δ-valerolactone), poly(γ-butyrolactone), poly(β-benzyl aspartate-co-aspartic acid), poly(γ-benzyl glutamate-co-glutaminic acid) and poly(α-amino acid), with (ii) a group represented by (1A), (1C) or (1D);

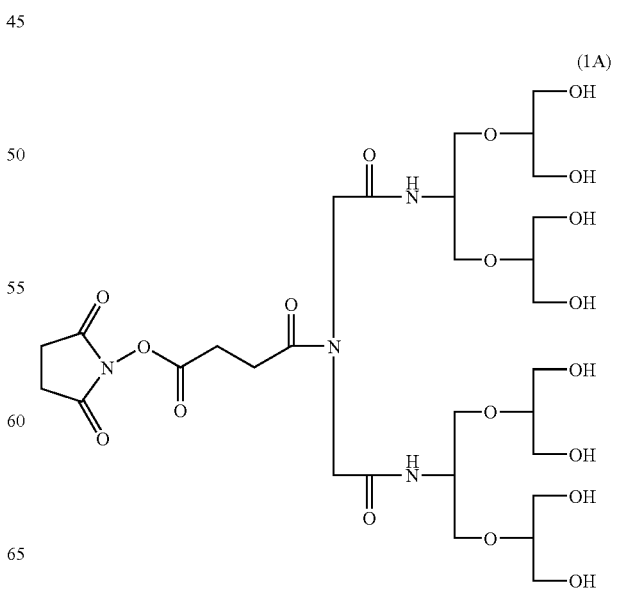

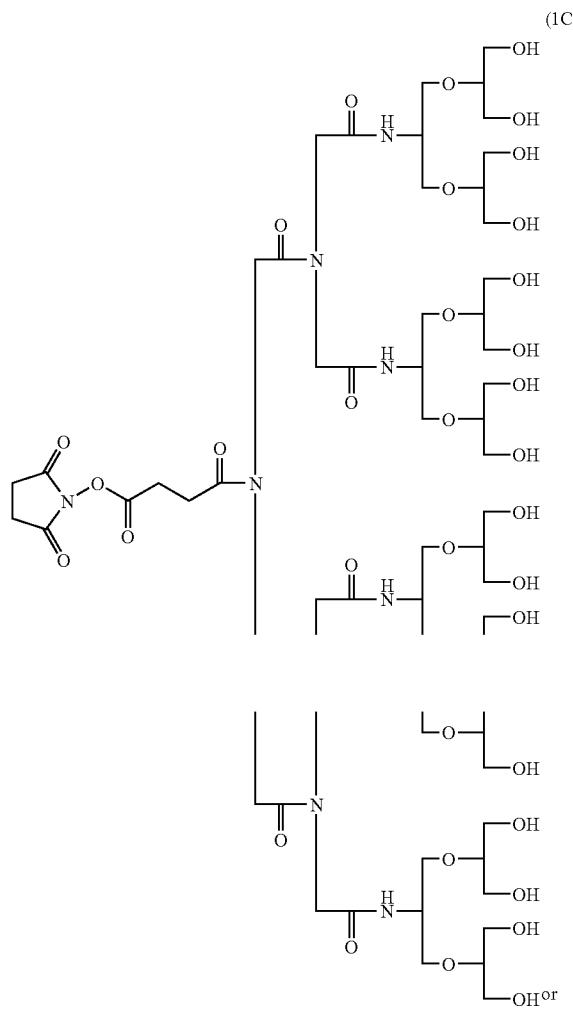

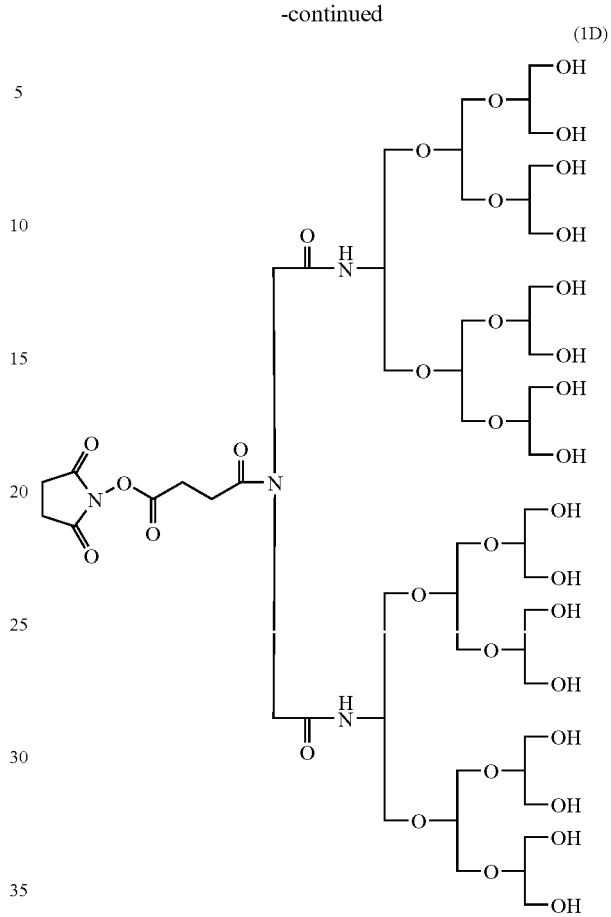

wherein the spacer is a straight-chain linking group selected from the group consisting of substituted or unsubstituted alkylene, carbonyl, substituted or unsubstituted imino, O, S and any combination thereof, or a salt thereof.

8. A fine particle comprising a compound of claim 7, or a salt thereof.

9. The fine particle according to claim 8, wherein the fine particle is selected from the group consisting of a liposome, a fat emulsion, an emulsion, a micell and a fine particle crystal.

* * * * *

UNITED STATES PATENT AND TRADEMARK OFFICE
CERTIFICATE OF CORRECTION

PATENT NO.       : 7,696,359 B2
APPLICATION NO.  : 10/570623
DATED            : April 13, 2010
INVENTOR(S)      : Hisao Nemoto et al.

It is certified that error appears in the above-identified patent and that said Letters Patent is hereby corrected as shown below:

COLUMN 1:

Line 34, "are" should read --show--.

COLUMN 26:

Line 15, "naphtyl" should read --naphthyl--.

COLUMN 29:

Line 64, "being transformed" should read --transforming--.

COLUMN 31:

Line 38, "chrolide" should read --chloride--.

COLUMN 33:

Line 34, "consisting" should read --consisting of--;
Line 47, "is" should read --are--;
Line 48, "is" should read --are--; and
Line 56, "is" should read --are--.

COLUMN 39:

Line 45, "chrolide" should read --chloride--; and
Line 65, "10 1093-1095" should read --10, 1093-1095--.

Signed and Sealed this

Twenty-second Day of June, 2010

David J. Kappos
*Director of the United States Patent and Trademark Office*

COLUMN 43:

Line 22, "1-yloxytris(pylidino)phosphonium" should read --1-yloxytris(pyridino)phosphonium--.

COLUMN 44:

Line 35, "romethan" should read --romethane--; and
   Line 36, "Compuond 6" should read --Compound 6--.

COLUMN 49:

Line 5, "shading" should read --shaking--.

COLUMN 53:

Line 40, ""C-NMR" should read --$^{13}$C-NMR--;
   Line 49, "chrolide" should read --chloride--;
   Line 56, ""C-NMR" should read --$^{13}$C-NMR--; and
   Line 61, "chrolide" should read --chloride--.

COLUMN 56:

Line 11, "chrolide" should read --chloride--; and
   Line 25, "337" should read --3.37--.

COLUMN 59:

Line 39, "chrolide" should read --chloride--; and
   Line 46, "δ 6 7.70-7.28" should read --δ 7.70-7.28--.

COLUMN 61:

Line 8, "chrolide" should read --chloride--;
   Line 10, "chrolide." should read --chloride.--; and
   Line 27, "com-" should read --Com- --.

CERTIFICATE OF CORRECTION (continued)
U.S. Pat. No. 7,696,359 B2

COLUMN 67:

Lines 4-41,

"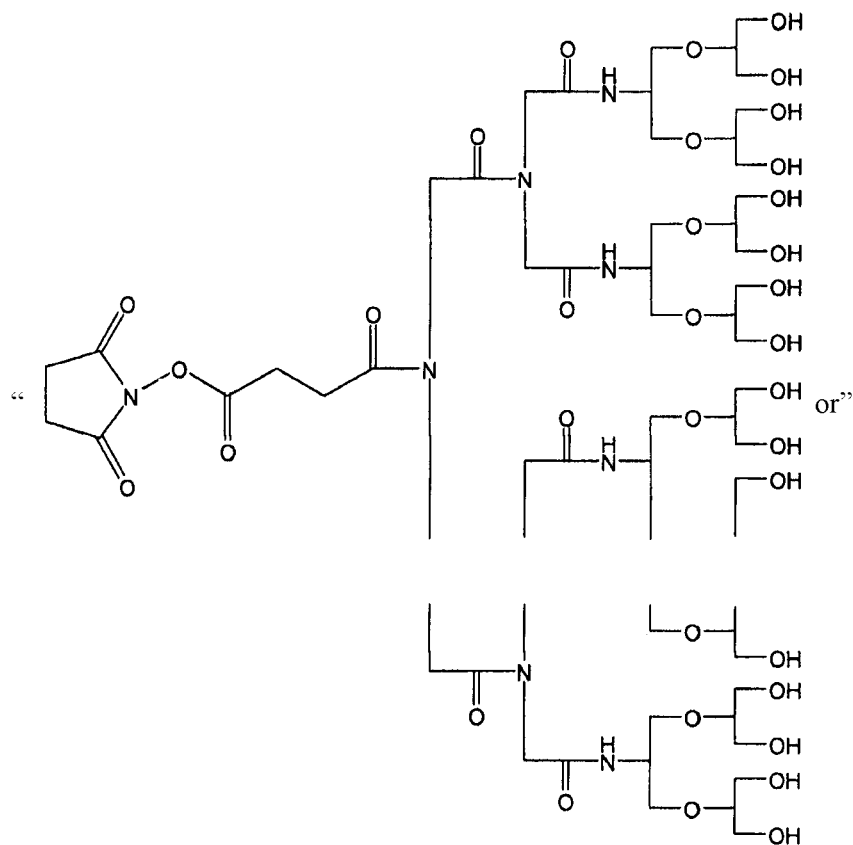 or"

CERTIFICATE OF CORRECTION (continued)
U.S. Pat. No. 7,696,359 B2 should read